(12) United States Patent
Wise et al.

(10) Patent No.: US 12,048,733 B2
(45) Date of Patent: *Jul. 30, 2024

(54) METHOD OF TREATMENT

(71) Applicants: THE BIONICS INSTITUTE OF AUSTRALIA, East Melbourne (AU); The University of Melbourne, Parkville (AU)

(72) Inventors: Andrew Wise, East Melbourne (AU); Robert K. Shepherd, East Melbourne (AU); Frank Caruso, Parkville (AU)

(73) Assignees: THE BIONICS INSTITUTE OF AUSTRALIA, East Melbourne (AU); THE UNIVERSITY OF MELBOURNE, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/824,654

(22) Filed: May 25, 2022

(65) Prior Publication Data

US 2022/0362337 A1    Nov. 17, 2022

Related U.S. Application Data

(63) Continuation of application No. 16/459,263, filed on Jul. 1, 2019, now Pat. No. 11,369,661, which is a continuation of application No. PCT/AU2018/051028, filed on Sep. 20, 2018.

(30) Foreign Application Priority Data

Sep. 20, 2017  (AU) ................. 2017903828
Sep. 20, 2017  (AU) ................. 2017903829
Jul. 11, 2018  (AU) ................. 2018902513

(51) Int. Cl.
| | | |
|---|---|---|
| *A61K 38/18* | (2006.01) | |
| *A61K 9/00* | (2006.01) | |
| *A61K 9/06* | (2006.01) | |
| *A61K 9/16* | (2006.01) | |
| *A61K 9/51* | (2006.01) | |
| *A61K 31/573* | (2006.01) | |
| *A61K 38/20* | (2006.01) | |
| *A61K 47/36* | (2006.01) | |
| *A61P 27/16* | (2006.01) | |
| *B82Y 5/00* | (2011.01) | |

(52) U.S. Cl.
CPC .......... *A61K 38/185* (2013.01); *A61K 9/0024* (2013.01); *A61K 9/0046* (2013.01); *A61K 9/06* (2013.01); *A61K 9/1611* (2013.01); *A61K 9/1652* (2013.01); *A61K 9/5115* (2013.01); *A61K 9/5161* (2013.01); *A61K 9/5192* (2013.01); *A61K 31/573* (2013.01); *A61K 38/2073* (2013.01); *A61K 47/36* (2013.01); *A61P 27/16* (2018.01); *B82Y 5/00* (2013.01)

(58) Field of Classification Search
CPC .. A61K 38/185; A61K 9/0024; A61K 9/0046; A61P 27/16
See application file for complete search history.

(56) References Cited

U.S. PATENT DOCUMENTS

| | | | |
|---|---|---|---|
| 4,468,498 | A | 8/1984 | Kowalski et al. |
| 5,157,084 | A | 10/1992 | Lee et al. |
| 5,521,253 | A | 5/1996 | Lee et al. |
| 11,369,661 | B2 | 6/2022 | Wise et al. |
| 2015/0202161 | A1 | 7/2015 | Pierstorff et al. |
| 2015/0252350 | A1 | 9/2015 | Kotov |
| 2020/0000879 | A1 | 1/2020 | Wise et al. |
| 2020/0253865 | A1 | 8/2020 | Wise et al. |

FOREIGN PATENT DOCUMENTS

| | | |
|---|---|---|
| CN | 104003404 A | 8/2014 |
| WO | WO-01/32760 A1 | 5/2001 |
| WO | WO-2006/037160 A1 | 4/2006 |
| WO | WO-2009/079688 A1 | 7/2009 |
| WO | WO-2015/051364 A1 | 4/2015 |
| WO | WO-2019/056062 A1 | 3/2019 |

OTHER PUBLICATIONS

Wang, Y. et al. "Mesoporous Silica Supraparticles for Sustained Inner-Ear Drug Delivery" Small 2014, 10, No. 21, 4244-4248 (Year: 2014).*
Maina, J.W. et al. "Mold-Templated Inorganic-Organic Hybrid Supraparticles for Codelivery of Drugs" Biomacromolecules 2014, 15, 4146-4151 (Year: 2014).*
Suzuki, J. et al. Round-window delivery of neurotrophin 3 regenerates cochlear synapses after acoustic overexposure. Sci. Rep. 6, 24907 (2016) (Year: 2016).*
Adamson, C.L. et al. "Opposite Actions of Brain-Derived Neurotrophic Factor and Neurotrophin-3 on Firing Features and Ion Channel Composition of Murine Spiral Ganglion Neurons" J. Neurosci., Feb. 15, 2002, 22(4):1385-1396 (Year: 2002).*
Miller, J.M. "Neurotrophins Can Enhance Spiral Ganglion Cell Survival After Inner Hair Cell Loss" Int. J. Devl Neuroscience, vol. 15, No. 4/5, pp. 631 643, 1997 (Year: 1997).*
Adamson et al., Opposite actions of brain-derived neurotrophic factor and neurotrophin-3 on firing features and ion channel composition of murine spiral ganglion neurons, J. Neurosci., 22(4):1385-96 (2002).
Clark et al., Surgery for an improved multiple-channel cochlear implant, Ann. Otol. Rhinol. Laryngol., 93(3 Pt 1):204-7 (May-Jun. 1984).
Clark et al., Surgical and safety considerations of multichannel cochlear implants in children, Ear Hear., 12(4 Suppl):15S-24S (Aug. 1991).

(Continued)

*Primary Examiner* — Andrew S Rosenthal
(74) *Attorney, Agent, or Firm* — MARSHALL, GERSTEIN & BORUN LLP

(57) ABSTRACT

The present invention relates to methods of treating an auditory disorder. In particular, the present invention relates to treating an auditory disorder using supraparticles comprising a therapeutic payload.

20 Claims, 15 Drawing Sheets

(56) References Cited

OTHER PUBLICATIONS

Figure 1A:
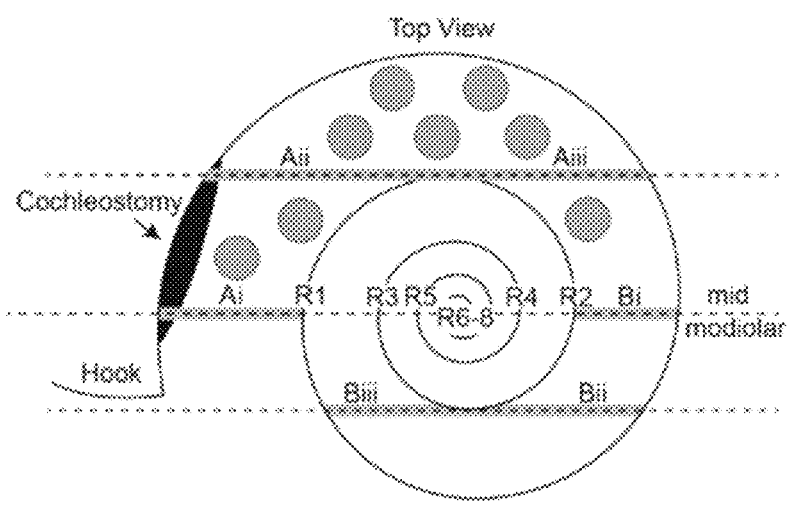

Cui et al., Engineering poly(ethylene glycol) particles for improved biodistribution, ACS Nano, 9(2):1571-80 (Feb. 2015).
Dobie, Audiometric threshold shift definitions: simulations and suggestions, Ear Hear, 26(1):62-77 (Feb. 2005).
Fallon et al., Functional Consequences of a Hidden Hearing Loss, Poster Session 928, at 40th Annual MidWinter Meeting, Association for Research in Otolaryngology, (Feb. 11-15, 2017).
Goldwyn et al., Modeling the electrode-neuron interface of cochlear implants: effects of neural survival, electrode placement, and the partial tripolar configuration, Hear Res., 268(1-2):93-104 (Sep. 2010).
International Application No. PCT/AU2018/051028, International Search Report and Written Opinion, mailed Oct. 5, 2018.
Jaworek, Micro- and nanoparticle production by electrospraying, Powder Technology, 176(1):18-35 (Jul. 2007).
Kuncicky et al., Sessile Droplet Templating of Miniature Porous Hemispheres from Colloid Crystals, Chem. Mater., 19(2):141-3 (2007).
Kuncicky et al., Surface-guided templating of particle assemblies inside drying sessile droplets, Langmuir, 24(4):1371-80 (Feb. 2008).
Landry et al., Spiral ganglion neuron survival and function in the deafened cochlea following chronic neurotrophic treatment, Hear Res., 282(1-2):303-13 (Dec. 2011).
Langer, New methods of drug delivery, Science, 249(4976):1527-33 (Sep. 1990).
Lee et al., Facile synthesis of mesoporous silica and titania supraparticles by a meniscus templating route on a suprhydrophobic surface and their application to adsorbents, Nanoscale, 6:3483 (2014).
Ma et al., Gel-Mediated Electrospray Assembly of Silica Supraparticles for Sustained Drug Delivery, ACS Appl. Mater. Interfaces, 10(37):31019-31 (2018).
Maina et al., Mold-templated inorganic-organic hybrid supraparticles for codelivery of drugs, Biomacromolecules, 15(11):4146-51 (Nov. 2014).
Miller et al., Neurotrophins can enhance spiral ganglion cell survival after inner hair cell loss, Int. J. Dev. Neurosci., 15(4-5):631-43 (1997).
Park et al., Direct-write fabrication of colloidal photonic crystal microarrays by ink-jet printing, J. Colloid Interface Sci., 298(2):713-9 (Jun. 2006).
Plontke et al., Concentration gradient along the scala tympani after local application of gentamicin to the round window membrane, Laryngoscope, 117(7):1191-8 (Jul. 2007).
Plontke et al., Dexamethasone Concentration Gradients Along Scala Tympani After Application to the Round Window Membrane, Otology & Neurotology, 29(3):401-6 (Apr. 2008).
Rastogi et al., Synthesis of Light-Diffracting Assemblies from Microspheres and Nanoparticles in Droplets on a Superhydrophobic Surface, Adv. Mater., 20(22):4263-8 (Nov. 2008).
Seyyedi et al., Within-subject comparison of word recognition and spiral ganglion cell count in bilateral cochlear implant recipients, Otol. Neurotol., 35(8):1446-50 (Sep. 2014).
Shepherd et al., Chronic depolarization enhances the trophic effects of brain-derived neurotrophic factor in rescuing auditory neurons following a sensorineural hearing loss, J. Comp. Neurol., 486(2):145-58 (May 2005).
Shepherd et al., Neurotrophins and electrical stimulation for protection and repair of spiral ganglion neurons following sensorineural hearing loss, Hear Res., 242(1-2):100-9 (Aug. 2008).
Suzuki et al., Round-window Delivery of Neurotrophin 3 Regenerates Cochlear Synapses After Acoustic Overexposure, Sci. Rep., 6:24907 (2016).
Tan et al., Nanoporous peptide particles for encapsulating and releasing neurotrophic factors in an animal model of neurodegeneration, Adv. Mater., 24(25):3362-6 (Jul. 2012).
Wang et al., Enzyme encapsulation in nanoporous silica spheres, Chem. Commun., 1528-9 (2004).
Wang et al., Hollow Carved Single-Crystal Mesoporous Silica Templated by Mesomorphous Polyelectrolyte-Surfactant Complexes, Chem. Mater., 22(13):3829-31 (2010).
Wang et al., Infiltration of macromolecules into nanoporous silica particles, Macromolecules, 40:7594-600 (2007).
Wang et al., Mesoporous silica spheres as supports for enzyme immobilization and encapsulation, Chem. Mater., 17:953-61 (2005).
Wang et al., Mesoporous silica supraparticles for sustained inner-ear drug delivery, Small, 10(21):4244-8 (Nov. 2014).
Wang et al., Nanoporous colloids: building blocks for a new generation of structured materials, J. Mater. Chem., 19:6451-64 (2009).
Wang et al., Nanoporous polyelectrolyte spheres prepared by sequentially coating sacrificial mesoporous silica spheres, 44(19):2888-92 (May 2006).
Wang et al., Nanoporous Protein Particles Through Templating Mesoporous Silica Spheres, Adv. Mater., 18(6):795-800 (Mar. 2006).
Wise et al., Combining cell-based therapies and neural prostheses to promote neural survival, Neurotherapeutics, 8(4):774-87 (Oct. 2011).
Wise et al., Drug delivery to the inner ear, J. Neural Eng., 9(6):065002 (2012).
Wise et al., Effects of localized neurotrophin gene expression on spiral ganglion neuron resprouting in the deafened cochlea, Mol. Ther., 18(6):1111-22 (Jun. 2010).
Wise et al., Improved Auditory Nerve Survival with Nanoengineered Supraparticles for Neurotrophin Delivery into the Deafened Cochlea, PLOS One, 11(10):e0164867 (2016).
Wise et al., Improved Auditory Nerve Survival with Nanoengineered Supraparticles for Neurotrophin Delivery into the Deafened Cochlea, PLoS One, 11(10):e0164867 (Oct. 2016).
Wise et al., Neurotrophin delivery using nanoengineered mesoporous silica particles for spiral ganglion neuron survival in the deaf cochlea, Poster and Abstract (PS-719), presented at the Association for Research in Otolaryngology 37th Annual Midwinter Meeting in San Diego, California (Feb. 22-26, 2014).
Wise et al., Resprouting and survival of guinea pig cochlear neurons in response to the administration of the neurotrophins brain-derived neurotrophic factor and neurotrophin-3, J. Comp. Neurol., 487(2):147-65 (Jun. 2005).
Wu et al., Efficient removal of heavy metal ions with biopolymer template synthesized mesoporous titania beads of hundreds of micrometers size, Environ. Sci. Technol., 46:419-25 (2012).
Xu et al., Profound hearing loss in the cat following the single co-administration of kanamycin and ethacrynic acid, Hear Res., 70(2):205-15 (Nov. 1993).
Yang et al., Reservoir-based polymer drug delivery systems, J. Lab. Autom., 17(1):50-8 (Feb. 2012).
Zhu et al., Cochlear-implant spatial selectivity with monopolar, bipolar and tripolar stimulation, Hear Res., 283(1-2):45-58 (Jan. 2012).
Zuccato et al., Brain-derived neurotrophic factor in neurodegenerative diseases, Nat. Rev. Neurol., 5(6):311-22 (Jun. 2009).
Rule 1.132 Declaration of Andrew Wise, Ph.D., dated Feb. 18, 2020, filed in U.S. Appl. No. 16/459,263 on Feb. 18, 2020.
Second Rule 1.132 Declaration of Andrew Wise, Ph.D., dated Sep. 4, 2020, filed in U.S. Appl. No. 16/459,263 on Sep. 8, 2020.

\* cited by examiner

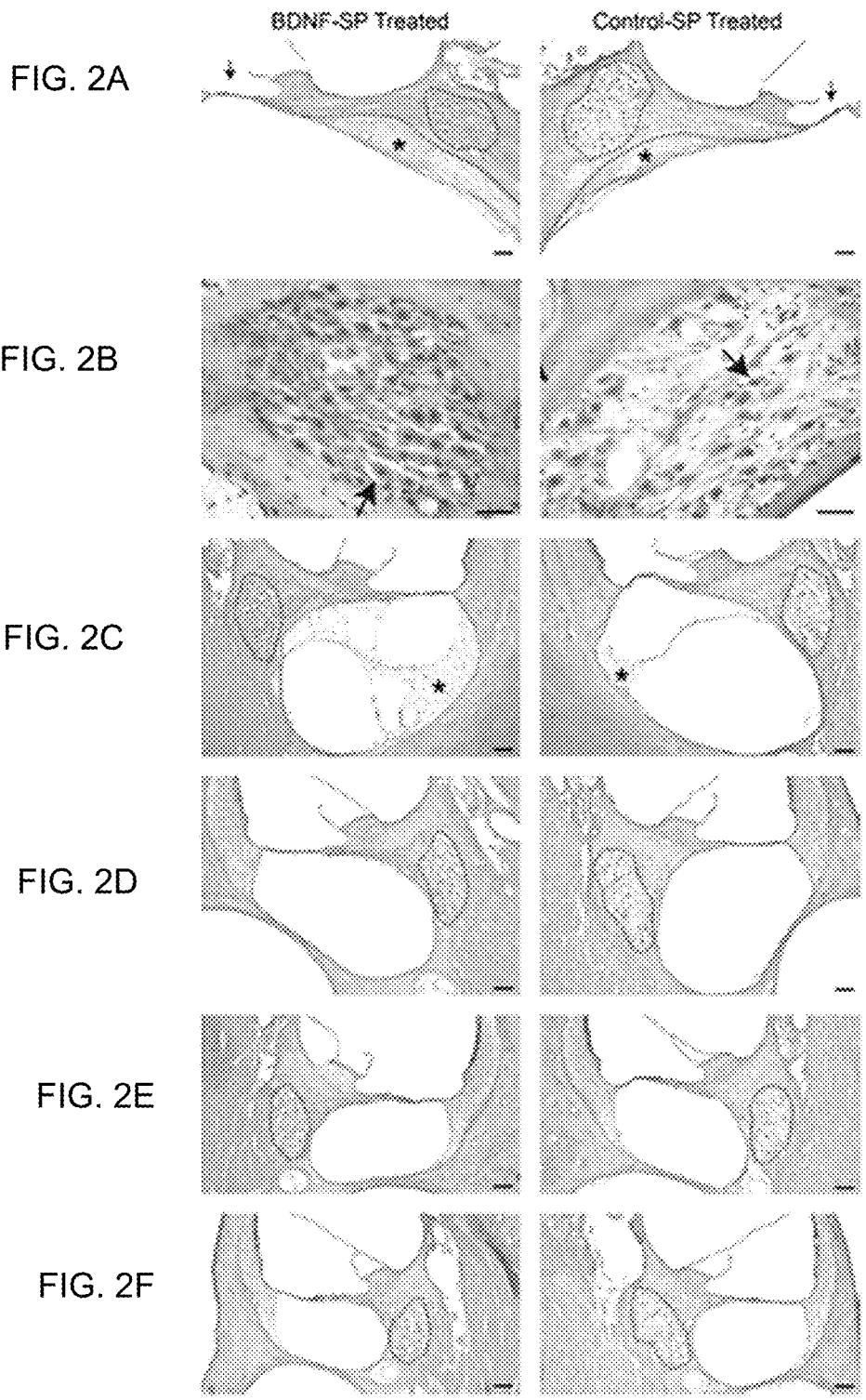

METHOD OF TREATMENT

CROSS-REFERENCE TO RELATED APPLICATIONS

This Application is a continuation of U.S. patent application Ser. No. 16/459,263, filed on Jul. 1, 2019, now U.S. Pat. No 11,369,661; which is a continuation of International Patent Application No. PCT/AU2018/051028, filed on Sep. 20, 2018; which claims priority from Australian Patent Application Nos. 2018902513, filed on Jul. 11, 2018; 2017903828, filed on Sep. 20, 2017; and 2017903829, filed on Sep. 20, 2017.

FIELD OF THE INVENTION

The present invention relates to methods of treating an auditory disorder. In particular, the present invention relates to treating an auditory disorder using supraparticles comprising a therapeutic payload.

BACKGROUND OF THE INVENTION

Hearing loss, a common side effect of many auditory disorders, is one of the most common sensory deficits affecting over 5.3% of people worldwide. Deafness can have a significant impact on communication in a hearing world and affect the development of language in children, with social and vocational implications throughout life.

Sensorineural hearing loss (SNHL) is the most common form of hearing loss and typically results from damage to the delicate sensory hair cells within the cochlea, or loss of their synaptic connections with spiral ganglion neurons (SGNs). SGNs are the target neurons for the cochlear implant, the only therapeutic option for people with profound to severe SNHL. Thus, a functional population of SGNs is essential for the implant to perform effectively. Accordingly, methods of enhancing survival of SGNs are required.

Methods of enhancing survival of SGNs are restricted by limitations of systemic delivery in crossing the blood-labyrinth barrier. Accordingly, previous methods have focused on administering therapeutics to the ear. Exogenous administration of neurotrophins using implantable mini-pumps has been shown to improve the survival of SGNs in animal deafness models. However, SGN survival is generally localised to the basal turn of the cochlea. Furthermore, the supply of neurotrophins from pump-based devices is finite, necessitating the need for pumps to be refilled or replaced and thus leading to concerns over the long-term safety of these devices.

A need therefore exists for a method of treating auditory disorders that supplies therapeutics in an effective manner.

SUMMARY OF THE INVENTION

The present inventors have surprisingly identified that supraparticles can deliver therapeutic compounds to the ear in sufficient quantities and over a sufficient duration to enhance cell survival along a wide extent of the tonotopic axis of the cochlea. The present inventors have also identified that supraparticle mediated delivery of therapeutic compounds to the inner ear can re-establish lost auditory synapses between auditory neurons and sensory hair cells. Accordingly, in a first example, the present disclosure relates to a method of treating an auditory disorder in a subject, the method comprising administering a supraparticle comprising a therapeutic payload. In another example, the present disclosure relates to a method of preventing an auditory disorder in a subject, the method comprising administering a supraparticle comprising a therapeutic payload.

In an example, the therapeutic payload is a neurotrophic factor. For example, the neurotrophic factor may be brain derived neurotrophic factor (BDNF), nerve growth factor, neurotrophin-3, neurotrophin-4, ciliary neurotrophic factor (CNTF), Glial Cell Derived Neurotrophic Factor (GDNF) and IL-11.

In an example, the supraparticle comprises at least 2, at least 3, at least 4, at least 5 different therapeutic payloads. For example, a supraparticle may comprise BDNF and a therapeutic payload selected from the group consisting of neurotrophin-3, neurotrophin-4, CNTF, GDNF, IL-11 and a steroid. In an example, the therapeutic payload is a steroid. For example, the steroid may be dexamethasone. In another example, the steroid is beclamthasone. In another example, the steroid is a corticosteroid. Other exemplary steroids include prednisone and Methylprednisolone.

In another example, the therapeutic payload may be a neurotransmitter. In another example, the therapeutic payload may be a neurotrophic factor. In another example, the therapeutic payload may be a neurotrophin. In another example, the therapeutic payload may be a virus. For example, the therapeutic payload may be an adenovirus. In another example, the therapeutic payload may be a stem cell. In an example, the supraparticle comprises at least two therapeutic payloads, one therapeutic payload being a neurotrophic peptide.

In another example, when performing the methods of the present disclosure, a supraparticle is administered to the subject's middle ear cavity. In another example, the supraparticle is administered onto the subjects round window or oval window. In another example, the supraparticle is administered by implantation into the subject's cochlea. In these examples, supraparticles may be administered to one of subject's ears. In another example, supraparticles may be administered to both ears of a subject.

In an example, at least two, at least three, at least four, at least 5, at least 10, at least 20 supraparticles may be administered to an ear of the subject. In this example, supraparticles may comprise different payloads. For example, a first supraparticle may comprise a first therapeutic payload and a second supraparticle comprises a different therapeutic payload that is a neurotrophic peptide. In an example, the first and second supraparticles comprise different neurotrophic peptides. In another example, the first supraparticle comprises a neurotrophic peptide and the second supraparticle comprises a steroid. In another example, the therapeutic payloads can target different receptors in the cochlea.

In another example, the methods of the present disclosure encompass administering supraparticles and implanting a cochlear device. In an example, the cochlear device is implanted simultaneously with the supraparticle(s). In another example, the cochlear device is implanted after the supraparticle(s) have been administered. For example, the cochlear device may be implanted about one month, about two months, about three months, about six months, about one to six months, about two to six months, about three to six months after the supraparticle(s) have been administered. In this example, additional supraparticles may be administered upon implantation of the cochlear device.

In an example, the supraparticles are at least about 50 µm, 100 µm, 200 µm, about 300 µm, about 400 µm, about 500 µm, about 600 µm, about 700 µm, about 800 µm, about 200 to 800 µm, about 300 to 700 µm, about 400 to 600 µm in size. In an example, the supraparticles have a bimodal pore structure.

In another example, each supraparticle comprises between about 0.1 µg and 2 µg of therapeutic payload. In another example, each supraparticle comprises at least 1 µg of therapeutic payload. In another example, each supraparticle comprises at least 2 µg of therapeutic payload.

In another example, supraparticle(s) are administered in a slow release formulation. In an example, the slow release formulation is a foam or a gel.

In an example, the auditory disorder is selected from the group consisting of hearing loss, tinnitus, Meniere's disease, bacterial ear infection, viral ear infection, hyperacusis and endolymphatic hydrops. In an example, the auditory disorder may be hearing loss. In an example, the hearing loss is characterised as sensorineural hearing loss (SNHL). In another example, the hearing loss is characterised as presbycusis, noise induced, disease induced, genetic, toxin induced or surgically induced. For example, the hearing loss is characterised as noise induced.

In an example, the hearing loss is characterised as noise induced SNHL. For example, hearing loss treated according to the methods of the present disclosure can be characterized as noise induced SNHL.

In another example, the hearing loss is characterised as disease induced. In an example, the disease induced hearing loss is induced by stroke, an autoimmune disease, Meniere's disease, viral infection, bacterial infection, osteosclerosis or cancer.

In another example, the hearing loss is characterised as genetic hearing loss. For example, the genetic hearing loss may result from down syndrome.

In another example, the hearing loss is characterised as toxin induced hearing loss. For example, the toxin induced hearing loss may result from drugs used to treat cancer.

In another example, the hearing loss is characterised as surgically induced hearing loss. For example, the surgically induced hearing loss may result from surgical implantation of a bionic device.

In an example, hearing loss treated or prevented by the methods according to the present disclosure is categorised as partial and progressive, severe or profound.

In another example, the present disclosure relates to use of a supraparticle comprising a therapeutic payload in the manufacture of a medicament for the treatment of an auditory disorder.

In another example, the present disclosure relates to a supraparticle comprising a therapeutic payload for use in a method of treating an auditory disorder.

In another example, the present disclosure relates to a method of treating hearing loss in a subject, the method comprising administering a supraparticle according to the present disclosure. For example, the hearing loss may be SNHL. In another example, the present disclosure relates to a method of treating noise induced hearing loss in a subject, the method comprising administering a supraparticle according to the present disclosure. In these examples, a supraparticle comprising a neurotrophin may be administered. For example, the supraparticle may comprise BDNF or neurotrophin-3. In an example, the supraparticle may comprise between 1.5 µg and 15 µg of neurotrophin. For example, the supraparticle may comprise between 1.5 µg and 15 µg of BDNF. In another example, the supraparticle may comprise between 1.5 µg and 15 µg of neurotrophin-3.

In an example, the present disclosure relates to use of a supraparticle comprising a therapeutic payload in the manufacture of a medicament for the treatment of hearing loss. In another example, the present disclosure relates to a supraparticle comprising a therapeutic payload for use in a method of treating hearing loss. In another example, the present disclosure relates to use of a supraparticle comprising a therapeutic payload in the manufacture of a medicament for the prevention of hearing loss. In another example, the present disclosure relates to a supraparticle comprising a therapeutic payload for use in a method of preventing hearing loss. In these examples, the hearing loss may be noise induced hearing loss. In other examples, the therapeutic payload is a neurotrophin.

Any example herein shall be taken to apply mutatis mutandis to any other example unless specifically stated otherwise.

The present invention is not to be limited in scope by the specific examples described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying drawings.

BRIEF DESCRIPTION OF THE
ACCOMPANYING DRAWINGS

Figure 1B:
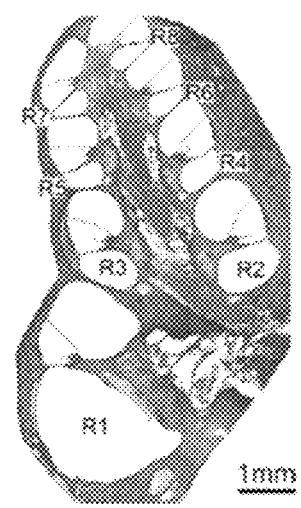

FIGS. 1A-1B (FIG. 1A) Schematic illustration of the top view looking down on the cochlea depicting the approximate location of the supraparticles (SPs; grey circles). The cochlear regions that were analysed for SGN density (region 1 to region 8; R1-R8) and tissue response to implantation (grey region on dotted lines—Ai-iii and Bi-iii) are shown. Tissue response data was averaged across i-iii for region A and B. (FIG. 1B) A mid modiolar micrograph of an implanted cochlea showing the cochlear regions in which SGN density within Rosenthal's canal was analysed (R1-R8).

FIGS. 2A-2F Representative examples of cochlear sections obtained from a cochlea treated with BDNF-SPs (left) and Control-SPs (right) for cochlear Regions 1-5 (FIGS. 2A-2F respectively). (FIG. 2A) shows the lower basal region (Region 1) with Rosenthal's canal outlined (dotted outline). There was a flattening of the sensory epithelium and complete loss of the organ of Corti (arrow) that was symmetrical between ears. There was a tissue response (*; Region Ai) to the presence of the SPs that was observed in the scala tympani with the bony wall depicted with a dotted line. (FIG. 2B) Higher magnification image of SGNs (arrows) in Rosenthal's canal in Region 1 from BDNF-SP treated cochlea (left) and from a Control-SP treated cochlea (right). There was a greater density of SGNs in the BDNF-SP treated cochlea compared to the control cochlea. (FIG. 2C) Cochlear section taken at Region 2 shows the Rosenthal's canal (dotted line) and the fibrotic tissue response (*; Region Bi) for the BDNF-SP (left) and Control-SP (right) cochleae. (FIGS. 2D-2F) Cochlear section taken at Region 3-5 shows the Rosenthal's canal (dotted line) for the BDNF-SP (left) and Control-SP (right) cochleae. There was no tissue response in these cochlear regions. Scale bar (FIG. 2A and FIGS. 2C-2F=100 μm) and (FIG. 2B=50 μm).

FIGS. 3A-3D Deterioration in auditory processing following synaptopathy (FIG. 3A) Example segments of acoustic stimulus (top row) and startle responses. Example psychometric function for a guinea pig illustrating an increase in suppression of the startle response with increasing modulation depth (see general methods). (FIG. 3B) There is a trend of increased modulation detection thresholds following synaptopathy. (FIG. 3C) Example acoustic stimulus (top row) and cycle-histograms (bottom row) of a single-unit recording (spike overlay inset) from the inferior colliculus. (FIG. 3D) There is a significant increase in modulation detection threshold following a synaptopathy (n=neurons).

Figure 4A:
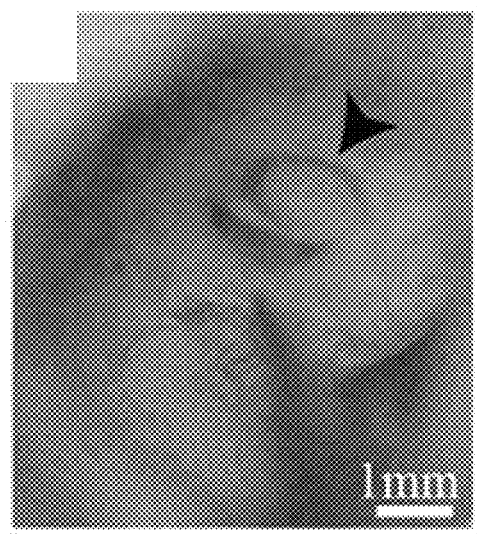
Figure 4B:
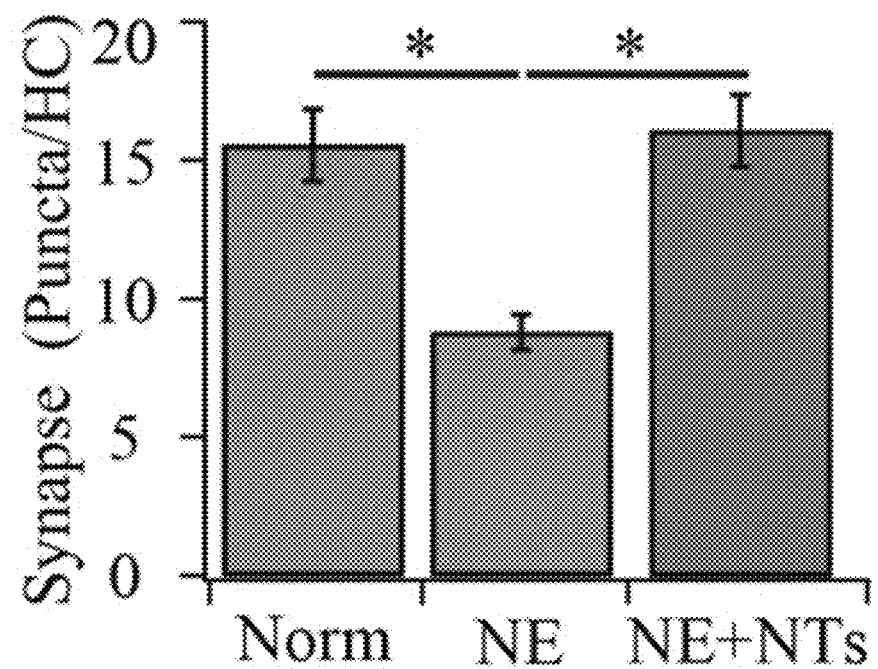

FIGS. 4A-4B (FIGS. 4A) Neurotrophin loaded supraparticles were delivered directly into the cochlea via a cochleostomy shortly after noise exposure (NE) (n=4). (FIGS. 4B) There was a significant (ANOVA, p <0.001) decrease in the number of ribbon synapses, compared to normal after 28 days post noise exposure which was completely reversed with neurotrophin treatment.

Figure 5A:
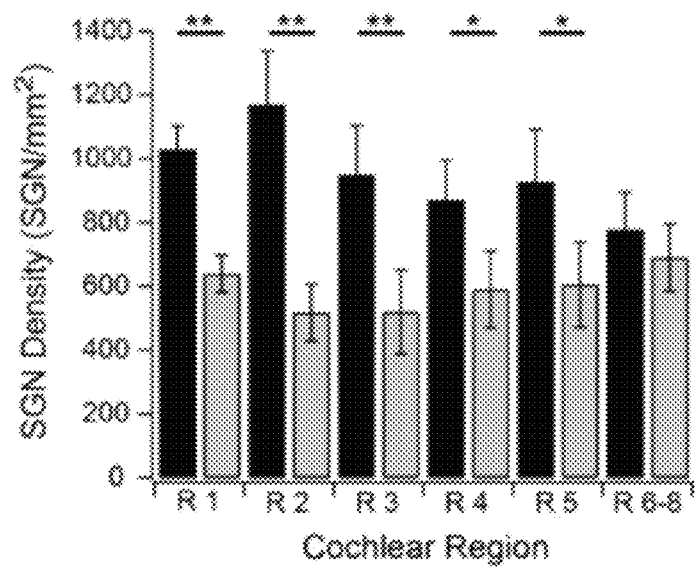
Figure 5B:
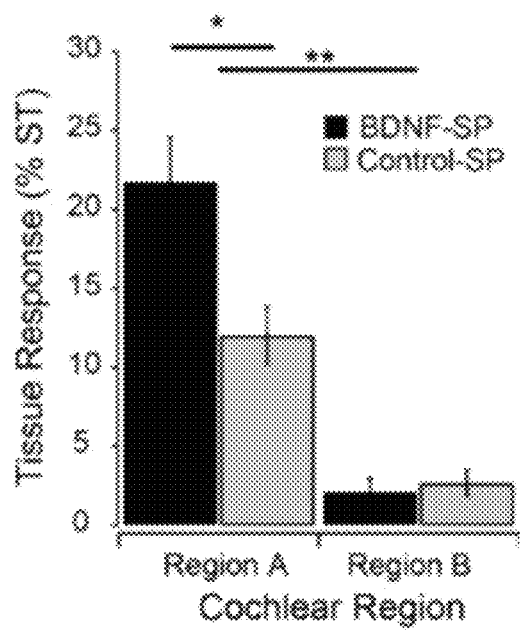

FIGS. 5A-5B Average of the SGN density measured in each cochlear region after one month of treatment with BDNF-SP (black) and the Control-SPs (Grey). There was a significantly greater density of SGNs in cochleae treated with BDNF-SPs compared to the Control-SPs (two way ANOVA, p<0.009) with post hoc analysis indicated (Holm-Sidak, **p<0.005, *p<0.05). Error bars ±1 SEM. (FIG. 5B) Analysis of the cochlear tissue response measured in the scala tympani (ST) in cochlear Regions A and B showed a tissue response for Region A (near the site of the cochleostomy) that was significantly larger than the tissue response in Region B (Post Hoc Holm-Sidak; p<0.001). The tissue response measured in Region A in the BDNF-SP treated cochleae was greater than that in the Control-SP treated cochlea (Post Hoc Holm-Sidak; p=0.003).

Figure 6:
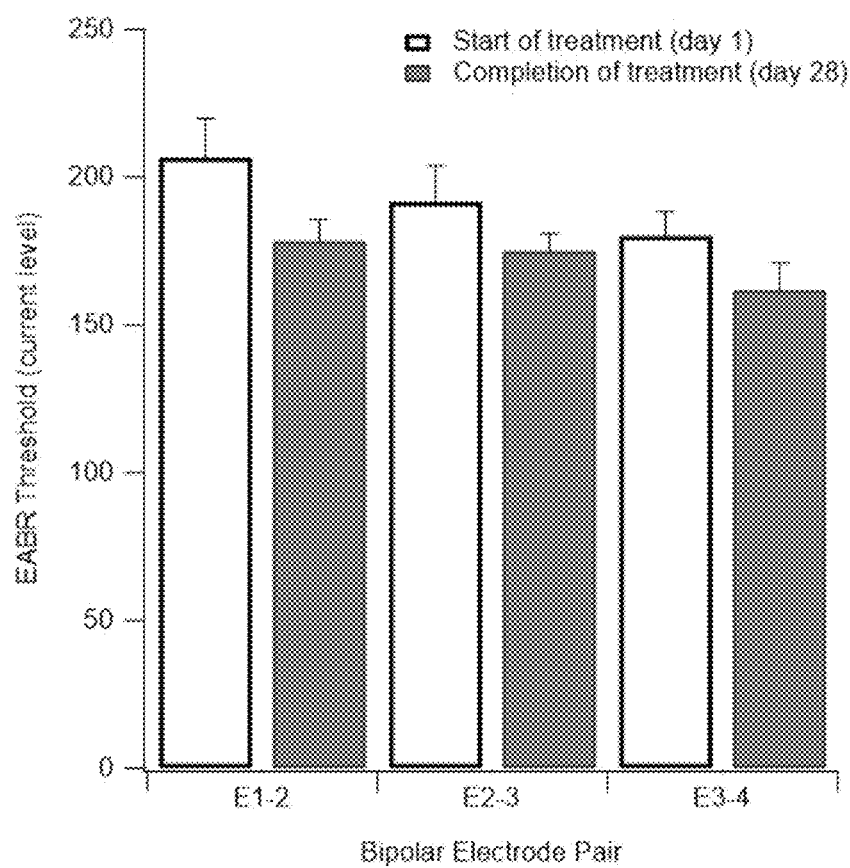

FIG. 6. Average (±SEM) electrically evoked auditory brainstem thresholds measured from n=3 animals following implantation of a cochlear implant containing 4 electrode contacts and control SPs (n=6 SPs each cochlea) into the basal turn of deafened guinea pigs. Electrical thresholds are shown for bipolar electrode pairs (E1-2, E2-3 and E3-4) that were measured immediately following implantation surgery and at the completion of the chronic stimulation treatment period (28 days). There was no statistically significant difference in thresholds (2 way RM ANOVA), with a trend of lower thresholds following treatment indicating that the SP system (control SPs—without drug) is safe to use in a cochlear implant model.

Figures 7A, 7B:
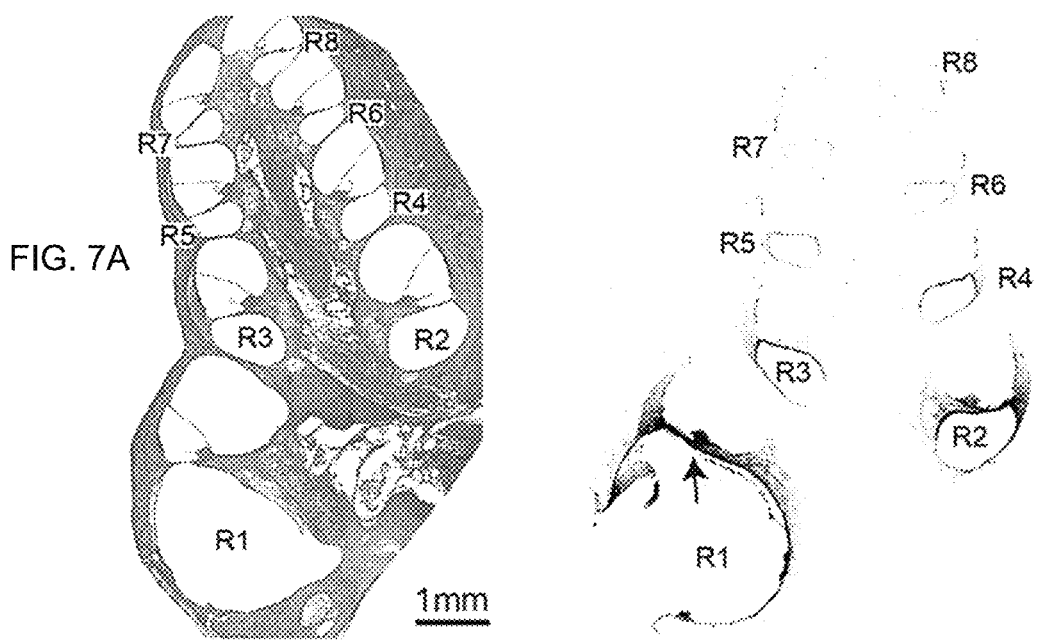
Figure 7C:
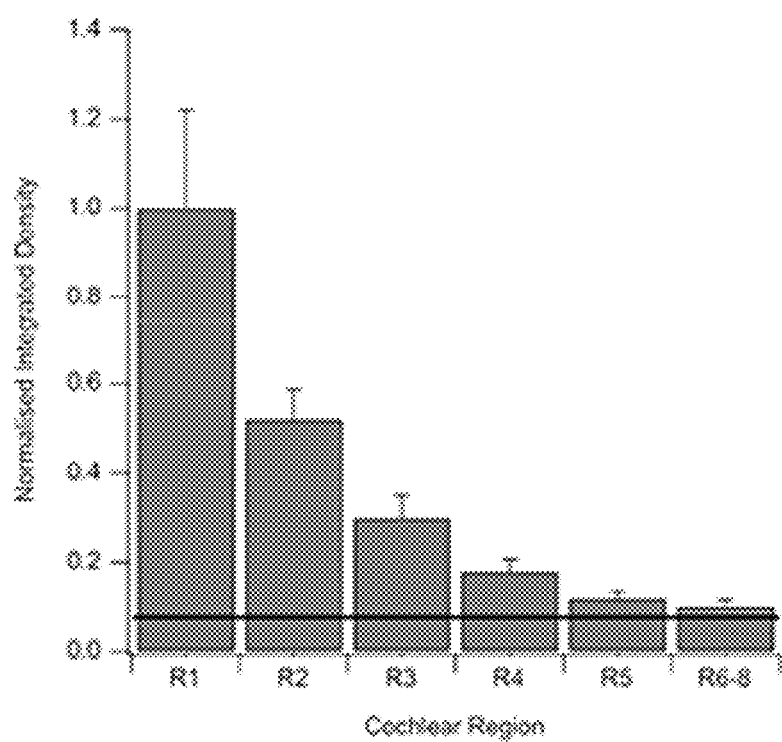

FIGS. 7A-7C FIG. 7A. Cochlear section from a chronically implanted animal depicting the cochlear regions from which spiral ganglion neurons were quantified. FIG. 7B. One SP loaded with NT3 (radiolabelled NT3) was implanted into the cochlea for 3 days. Cochlear section processed for autoradiography showing the distribution of the radiolabelled neurotrophin (depicted as black staining). Signal was detected throughout the cochlea indicating that the supraparticles could deliver neurotrophins to a wide extent of the cochlea. FIG. 7C. Quantification of cochlear autoradiography shows the relative proportion of neurotrophin distribution throughout the cochlea following 3 days of implantation of one supraparticle loaded with radiolabelled neurotrophin-3. Signal (above background levels as shown by the line) was evident in all but the most apical cochlear regions.

Figure 8:
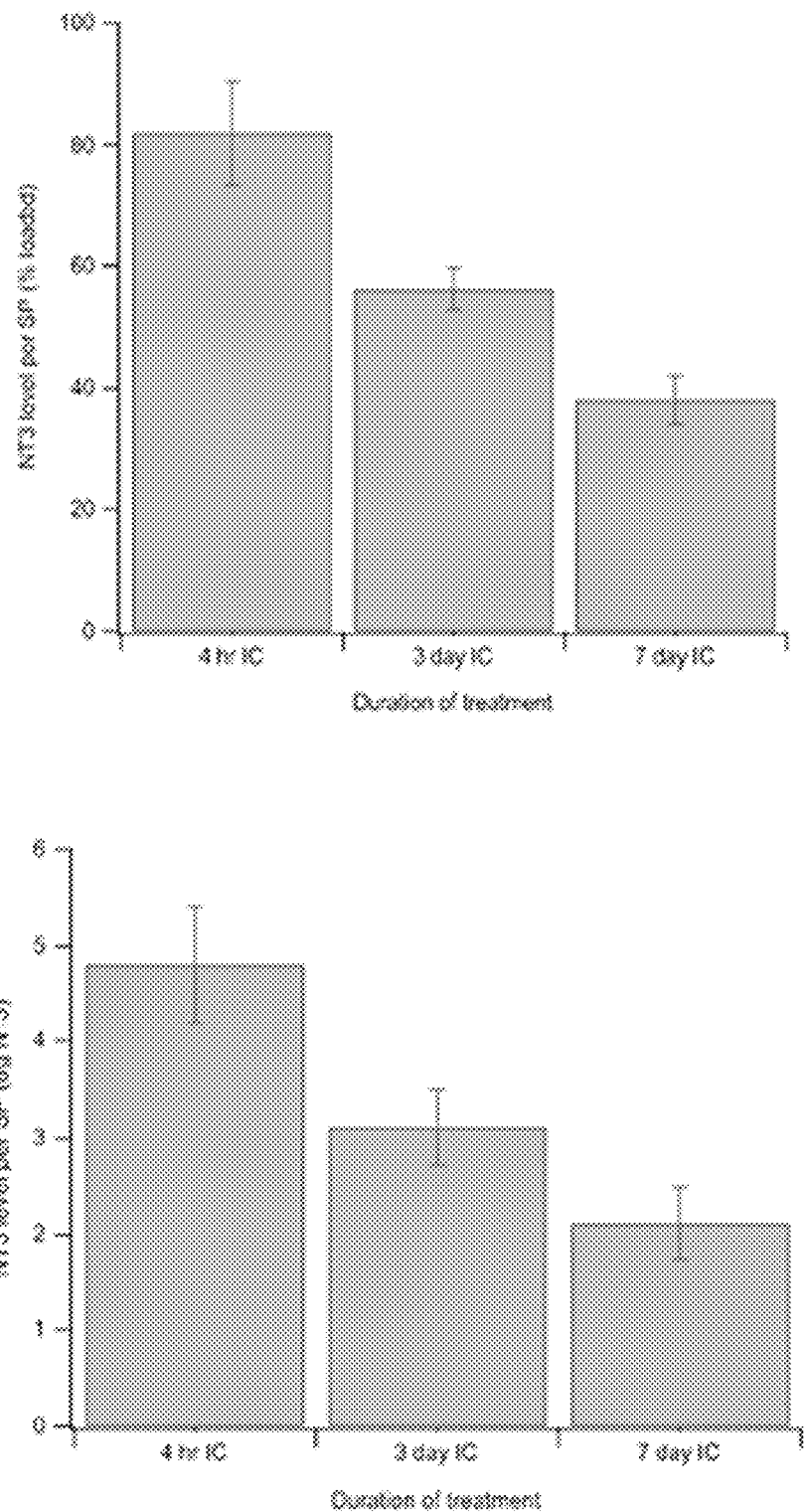

FIG. 8. Amount of neurotrophin-3 (% of loaded) and the total in μg is shown. After 1 week of implantation each SP contained ~2ug of neurotrophin-3 (~40%) of initial loaded amount.

Figure 9:
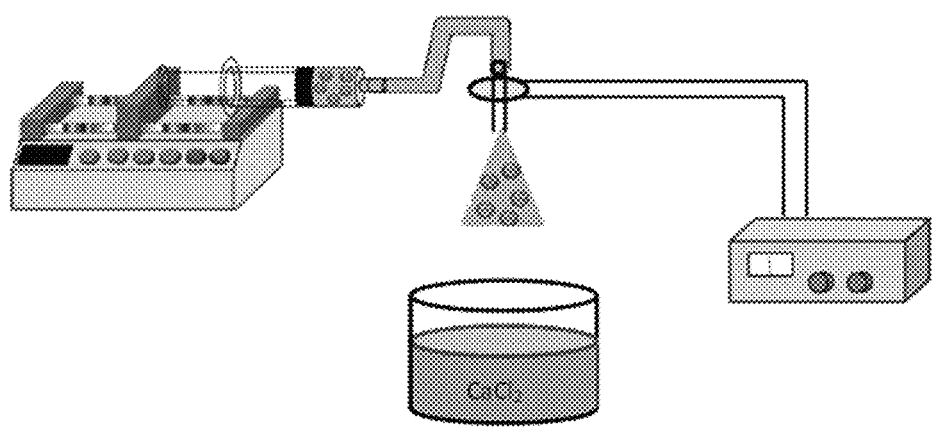

FIG. 9. A procedure for making MS-SPs.

FIGS. 10A-10D. Drug loading after 3 days (72 h) incubation time using different FITC-lysozyme loading concentration. (FIG. 10A) The adsorbed amount of FITC-lysozyme into non-porous MS-SPs$^{alg}$ (black circles), small pore MS-SPs$^{alg}$ (squares) and MS-SPs$^{alg}$ (triangles) versus the FITC-lysozyme loading concentration. (FIG. 10B) The adsorbed amount of FITC-lysozyme into non-porous MS-SPs (black circles), small pore MS-SPs (squares) and MS-SPs (triangles) versus the FITC-lysozyme loading concentration. (FIG. 10C) The FITC-lysozyme loading efficiency in MS-SPs$^{alg}$ and d) MS-SPs. Data presented is average of three replicates, each using five SPs, and error bars represent standard deviation.

Figure 11A:
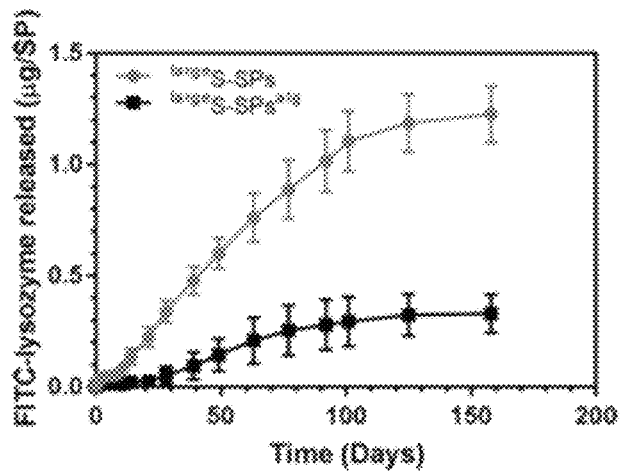
Figure 11B:
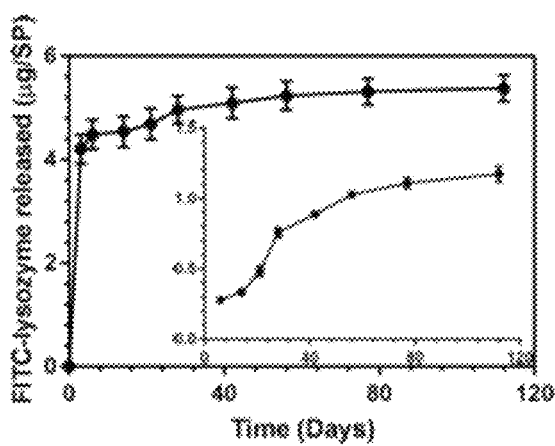
Figure 11C:
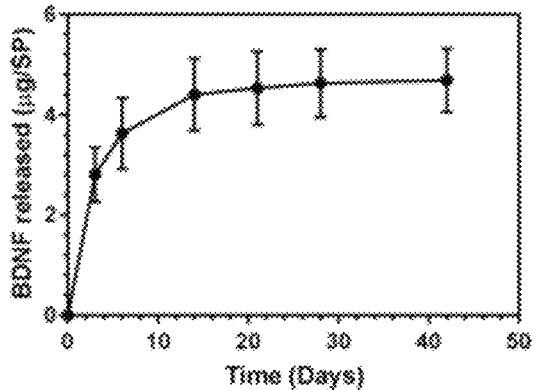

FIGS. 11A-11C. In-vitro cumulative drug release profile. (FIG. 11A) In-vitro FITC-lysozyme (0.2 mg mL$^{-1}$, drug loading for 3 days) release from MS-SPs (circle), and MS-SPs$^{alg}$ (black triangle). Data presented is average of three replicates, each using ten SPs, and error bars represented standard deviation. (FIG. 11B) In-vitro FITC-lysozyme (1.0 mg mL$^{-1}$, drug loading for 3 days) release from MS-SPs. The inset in (FIG. 11B) is the in-vitro FITC-lysozyme release profile starting from 6 days. (FIG. 11C) In-vitro BDNF release from MS-SPs (1.0 mg mL$^{-1}$, drug loading for 3 days). BDNF ELISA (Abcam) was used for the measurement of BDNF concentration.

Figure 12:
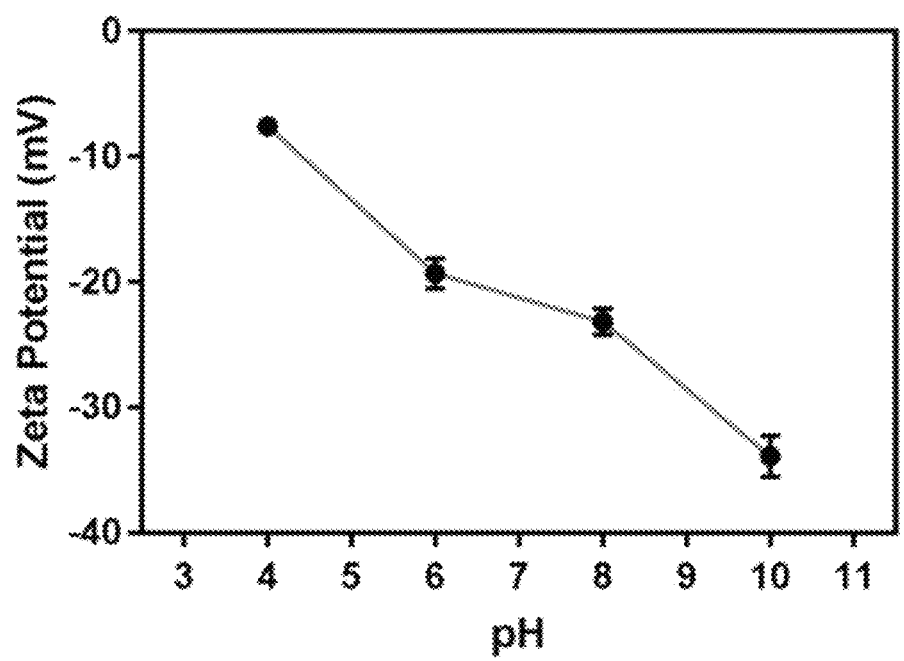

FIG. 12. Zeta potential of MS-SPs as a function of different pH values. Zeta potential measurements were carried out in 10 mM sodium acetate buffer (pH 4), 10 mM phosphate buffer (pH 6), 10 mM HEPES buffer (pH 8) and 10 mM sodium bicarbonate buffer (pH 10).

Figures 13A, 13B, 13C:
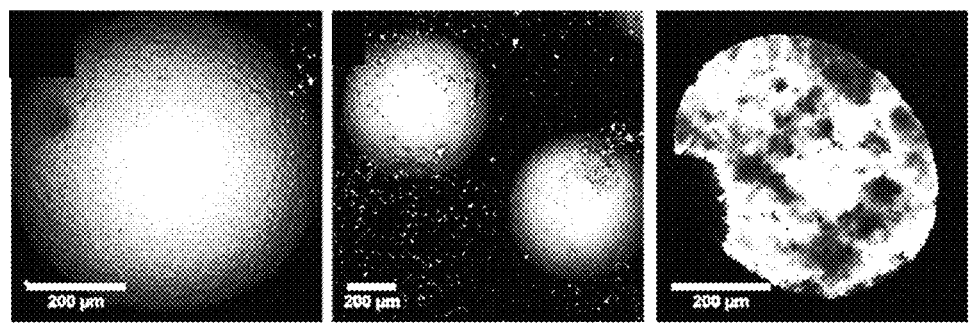
Figure 14A:
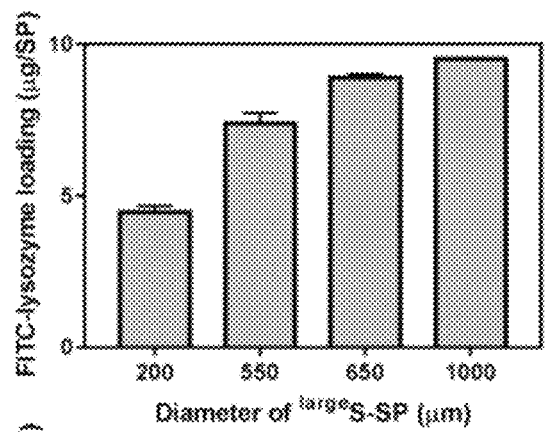
Figure 14B:
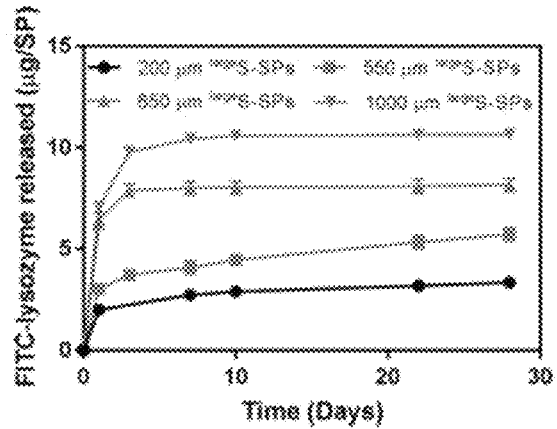
Figure 14C:
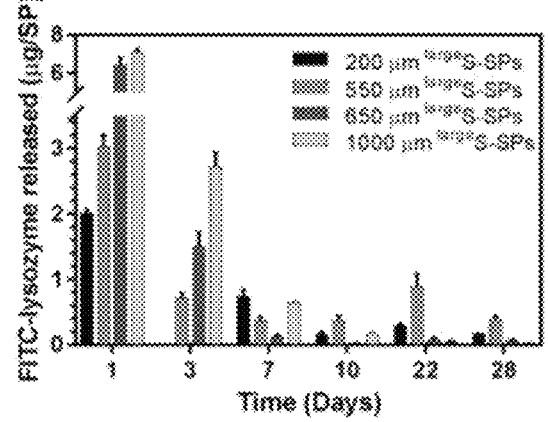
Figure 14D:
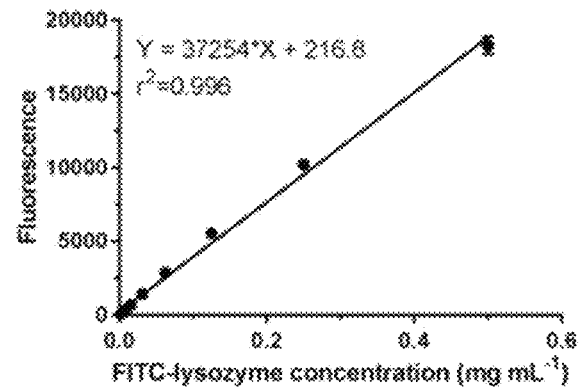

FIGS. 13A-13C. Confocal microscopy images of MS-SPs loaded with FITC-lysozyme (green). (FIGS. 13A and 13B) MS-SPs at different magnifications. (FIG. 13C) Inside of a fragmented MS-SP loaded with FITC-lysozyme.

FIGS. 14A-14D. FITC-lysozyme loading and release behaviour from MS-SPs with different diameters. (FIG. 14A) FITC-lysozyme loading amount, (FIG. 14B) In-vitro FITC-lysozyme release profile, (FIG. 14C) the value of FITC-lysozyme released at each individual time point, (FIG. 14D) In-vitro FITC-lysozyme release standard curve from MS-SPs with the diameter of 200, 550, 650, 1000 μm.

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., physiology, molecular biology and biochemistry).

As used in this specification and the appended claims, terms in the singular and the singular forms "a," "an" and "the," for example, optionally include plural referents unless the content clearly dictates otherwise. Thus, for example, reference to "a supraparticle" optionally includes a plurality of supraparticles.

As used herein, the term "about", unless stated to the contrary, refers to +/−10%, more preferably +/−5%, more preferably +/−1%, of the designated value.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "treatment" refers to clinical intervention designed to alter the natural course of the individual or cell being treated during the course of clinical pathology. Exemplary desirable effects of treatment include reduction in symptoms associated with an auditory disorder being treated. In the context of Meniere's disease, treatment may improve hearing and/or reduce tinnitus or vertigo. In the context of tinnitus, treatment may reduce ringing or other perceived noise in the ear(s) of the subject. In the context of hearing loss, desirable effects of treatment include decreasing the rate of hearing loss and/or ameliorating or palliating hearing loss. An individual is successfully "treated", for example, if one or more symptoms associated with the auditory disorder are mitigated or eliminated. Further exemplary desirable effects of treatment include improved growth or survival of cells from the auditory system such as neurons in the inner or middle ear or their synaptic connections.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated. In one example, treatment is associated with enhance cell survival along a wide extent of the tonotopic axis of the cochlea. In another example, treatment is associated with re-establishment of lost auditory synapses between auditory neurons and hair cells. In another example, treatment is associated with re-establishment of lost auditory synapses between cells in the cochlea.

As used herein, the term "prevention" includes providing prophylaxis with respect to occurrence of a disease in an individual. An individual may be predisposed to or at risk of developing the disease but has not yet been diagnosed with the disease. For example, the methods of the present disclosure may be used to prevent hearing loss in an individual following exposure to a stimulus or substance known to induce an auditory disorder.

A "therapeutically effective amount" is at least the minimum amount required to effect a measurable improvement of a particular disorder (e.g. hearing loss). For example, reference to a therapeutically effective amount in the context of the present disclosure can be used to describe an amount that enhances growth or survival of neurons or synaptic connections in the cochlea, or protection, repair and or regeneration of cochlear hair cells. A therapeutically effective amount can also include at least the minimum amount required to effect a measurable improvement in a subjects hearing. A therapeutically effective amount can be provided in one or more administrations. The therapeutically effective amount may vary according to the severity of hearing loss being treated and also according to the weight, age, racial background, sex, health and/or physical condition. Typically, the effective amount will fall within a relatively broad range (e.g. a "dosage" range) that can be determined through routine trial and experimentation by a medical practitioner. The therapeutically effective amount can be administered in a single dose or in a dose repeated once or several times over a treatment period.

Treatment and Prevention

The methods of the present disclosure are directed towards the treatment and/or prevention of an auditory disorder in a subject. The term "auditory disorder" is used in the context of the present disclosure to refer to disorders causing an inability to differentiate, recognize or understand sounds. Exemplary auditory disorders include hearing loss, tinnitus and diseases of the middle ear, inner ear and vestibular system such as Meniere's disease, bacterial and viral ear infections, hyperacusis and endolymphatic hydrops. In an example, the term auditory disorder is used to refer to disorders characterised by loss of neurons and/or hair cells or their synaptic connections in the inner ear and/or middle ear disorders.

In an example, the methods of the present disclosure encompass treating or preventing injury or degeneration of cells from the ear which cause auditory disorders such as hearing loss and/or vestibular symptoms such as nausea, dizziness, imbalance and vertigo. In an example, the methods of the present disclosure encompass treating auditory disorders by enhancing growth or survival of cells from the auditory system such as neurons or their synaptic connections. Examples include cells located in the middle ear, inner ear and vestibular system. In an example, the methods of the present disclosure encompass treating or preventing auditory disorders by enhancing growth or survival of cells such as SGNs, hair cells, including inner and outer ear hair cells, cochlear glial cells and Schwann cells. Exemplary synaptic connections treated according to the present disclosure include connections between hair cells, hair cells and SGNs or other neurons discussed above.

Accordingly, in an example, the methods of the present disclosure can be used to enhance growth or survival of hair cells. In an example, the methods of the present disclosure can be used to regenerate hair cells. For example, these methods can comprise administering a supraparticle according to the present disclosure loaded with a neurotrophin.

In an example, the methods of the present disclosure enhance growth or survival of neurons or synaptic connections in the cochlea. For example, the present methods can enhance growth or survival of neuronal cell bodies in Rosenthal's canal or their synaptic connections (see FIGS. 1A-1B Region 1-Region 8). In another example, the present methods enhance growth or survival of neurons or synaptic connections in the upper middle cochlear regions (FIGS. 1A-1B, Region 1-Region 5). Put another way, the present methods can enhance growth or survival of neurons in any one or more of Region 1, Region 2, Region 3, Region 4, Region 5, Region 6, Region 7 and Region 8 of Rosenthal's canal. In other examples, the present methods enhance growth or survival of neurons in Region 1-Region 2, Region 1-Region 3, Region 1-Region 4, Region 1-Region 5, Region 1-Region 6, Region 1-Region 7 or Region 1-Region 8 of Rosenthal's canal. In another example, the present methods can enhance growth or survival of nerve fibres in osseous spiral lamina.

In another example, the present methods enhance growth or survival of neurons or synaptic connections in at least 50% of the cochlea. In another example, supraparticles enhance growth or survival of neurons or synaptic connections in at least 60%, at least 70%, at least 80%, at least 90%, at least 95% of the cochlea.

The methods of the present disclosure are also directed towards the treatment or prevention of hearing loss in a subject. The term "hearing loss" is used in the context of the present disclosure to refer to any reduction in a subject's ability to detect sound. Thus, reference to hearing loss encompasses a partial or total inability to hear.

In an example, hearing loss treated according to the methods of the present disclosure may be characterised as sensorineural hearing loss (SNHL). SNHL is used in the context of the present disclosure to refer to hearing loss resulting from damage to the delicate sensory hair cells within the cochlea, damage to the spiral ganglion neurons (SGNs) or loss of the synaptic connections between hair cells and SGNs.

In an example, hearing loss treated according to the methods of the present disclosure is characterised as presbycusis. In another example, the hearing loss is noise induced. Exemplary causes of noise induced hearing loss include exposure to loud noises, acoustic trauma (injury caused by sudden loud noise) or blast injury. In other examples, the hearing loss can be disease induced, toxin or drug induced, trauma induced or genetic. For example, disease induced hearing loss can be induced by stroke, an autoimmune disease, viral infections such as meningitis, mumps, measles, or suppurative labyrinthitis, viral infections of the inner ear such as herpes simplex or cytomegalovirus, viral infections of the auditory nerve, bacterial infection such as lyme disease or syphilis, osteosclerosis or cancer. Exemplary trauma induced hearing loss includes vasculitis, inner ear barotraumas such as those caused by diving or acute pressure changes, physical trauma such as fracture of the temporal bone affecting the cochlea and middle ear, congenital defect, or surgical trauma resulting from surgical intervention in the inner ear. For example, trauma induced hearing loss can result from surgical implantation of a bionic device. Such trauma can present immediately after surgery and/or as delayed trauma weeks or months after surgery. In an example, the present disclosure encompasses methods of treating trauma induced hearing loss occurring immediately after implantation of a bionic device and trauma induced hearing loss occurring weeks or months after implantation of a bionic device.

Various exemplary toxins or drugs result in hearing loss that may be treated according to the present disclosure. Examples include chemical or pharmaceutical agents such as antineoplastic agents including cisplatinum or related compounds, antibiotics including aminoglycosides such as tobrahmycin or related compounds, loop diuretics such as furosemide, antimetabolites such as methotrexate, salicylates such as aspirin and therapeutic radiation. Exemplary genetic causes of hearing loss include down syndrome and Usher's syndrome. In another example, the hearing loss is conductive hearing loss. In other examples, the hearing loss is high frequency or low frequency hearing loss.

One of skill in the art will appreciate that hearing loss can be defined in different ways. For example, hearing loss can be defined based on hearing loss range in decibels (dB). In one example, hearing loss is defined as a 10 dB standard threshold shift or greater in hearing sensitivity for two of 6 frequencies ranging from 0.5-6.0 kHz (i.e. 0.5, 1, 2, 3, 4, 5 and 6 kHz; see for e.g. Dobie, R.A. (2005) Audiometric Threshold Shift Definitions: Simulations and Suggestions, Ear and Hearing 26(1) 62-77). Low frequency hearing can be defined as hearing loss at two adjacent low frequencies (0.5-2 kHz), or 10 dB at any frequency below 2 kHz. High frequency hearing loss can be defined as 5 dB hearing loss at two adjacent high frequencies (2-6 kHz), or 10 dB at any frequency above 2 kHz.

In another example, hearing loss can be defined based on a subject's ability to detect sound in dB. For example, mild hearing loss may be characterised as hearing from about 16 to about 25 dB. These subjects may have difficulty following speech in noisy situations. Moderate hearing loss may be characterised as hearing from about 40 to about 69 dB. These subjects may have difficulty following speech without a hearing aid. In another example, severe hearing loss may be characterised hearing from about 70 to about 89 dB. These subjects require powerful hearing aids or an implant. In another example, profound hearing loss may be characterised as hearing from about 90 dB. These subjects rely mainly on lip-reading and/or sign language, or an implant.

Hearing loss determinations can be made using for example, method of limits, method of constant stimuli, method of adjustment, forced choice methods, staircase or "up-down" methods or Bekesy's tracking method. Various other methods are known in the art for detecting and characterising severity of hearing loss. General screening can comprise speech recognition or tuning fork tests. Other screening methods can comprise audiometer tests in which a subject is presented with a range of sounds of various tones. In another example, severity of hearing loss can be determined in relation to the absolute threshold of hearing (ATH). Another exemplary method of determining the extent of hearing loss includes assessing perception of speech in noise or temporal processing including assessing detection of amplitude modulated sounds. In the context of patients with a cochlear implant, hearing may be measured by assessing auditory responses with an electrode array in response to electrical or acoustic stimuli.

Treating hearing loss according to the present disclosure may result in an improvement in a subjects hearing. For example, a subjects ability to detect sound in dB may improve. In another example, treating hearing loss reduces the progression of hearing loss. Treatment outcomes can be assessed using the methods of detecting hearing loss discussed above. In some cases it may be desirable to repeat hearing assessments over time to track treatment of hearing loss. For example, hearing loss can be compared before and after treatment to determine whether a subjects hearing has improved. In another example, hearing loss can be monitored periodically such as every one, two or three months over a period of time such as 6 months, a year or two years to determine whether a subjects hearing has improved.

Supraparticles

The term "supraparticle" ("SP") is used in the context of the present disclosure to refer to agglomerated particles comprising a network of pores. The network of pores provides supraparticles with a large pore volume and surface area for carrying a therapeutic payload. A large pore volume and surface area is advantageous as it can enhance the amount of therapeutic payload that can be carried by supraparticles. In an example, supraparticles according to the present disclosure are agglomerated nanoparticles.

In an example, supraparticles according to the present disclosure comprise at least 1.5 µg of therapeutic payload. In another example, supraparticles comprise at least 2.0 µg of therapeutic payload.

In another example, supraparticles according to the present disclosure comprise at least 2.5 µg of therapeutic payload. In another example, supraparticles comprise at least 2.6 µg of therapeutic payload. In another example, supraparticles comprise at least 2.7 µg of therapeutic payload. In another example, suprapartides comprise at least 2.7 µg of therapeutic payload. In another example, suprapartides comprise at least 2.8 µg of therapeutic payload. In another example, suprapartides comprise at least 2.9 µg of therapeutic payload. In another example, suprapartides comprise at least 3.0 µg of therapeutic payload. In another example, suprapartides comprise at least 3.1 µg of therapeutic payload. In another example, suprapartides comprise at least 3.2 µg of therapeutic payload. In another example, suprapartides comprise at least 3.3 µg of therapeutic payload. In another example, suprapartides comprise at least 3.4 µg of therapeutic payload. In another example, suprapartides comprise at least 3.5 µg of therapeutic payload. In another example, suprapartides comprise at least 3.6 µg of therapeutic payload. In another example, suprapartides comprise at least 3.7 µg of therapeutic payload. In another example, suprapartides comprise at least 3.8 µg of therapeutic payload. In another example, suprapartides comprise at least 3.9 µg of therapeutic payload. In another example, suprapartides comprise at least 4.0 µg of therapeutic payload. In another example, suprapartides comprise at least 4.5 µg of therapeutic payload. In another example, suprapartides comprise at least 5.0 µg of therapeutic payload. In another example, suprapartides comprise at least 5.5 µg of therapeutic payload. In another example, suprapartides comprise at least 6.0 µg of therapeutic payload. In another example, suprapartides comprise at least 6.5 µg of therapeutic payload. In another example, suprapartides comprise at least 7.0 µg of therapeutic payload. In another example, suprapartides comprise at least 7.5 µg of therapeutic payload. In another example, suprapartides comprise at least 8.0 µg of therapeutic payload. In another example, suprapartides comprise at least 8.5 µg of therapeutic payload. In another example, suprapartides comprise at least 9.0 µg of therapeutic payload. In another example, suprapartides comprise at least 9.5 µg of therapeutic payload. In another example, suprapartides comprise at least 10 µg of therapeutic payload. In another example, suprapartides comprise at least 10.5 µg of therapeutic payload. In another example, suprapartides comprise at least 11 µg of therapeutic payload. In another example, suprapartides comprise at least 11.5 µg of therapeutic payload. In another example, suprapartides comprise at least 12 µg of therapeutic payload. In another example, suprapartides comprise at least 15 µg of therapeutic payload. In another example, suprapartides comprise at least 20 µg of therapeutic payload.

For example, suprapartides can comprise at least 6 µg of therapeutic payload. In another example, suprapartides can comprise between about 2.5 and 10 µg of therapeutic payload. In another example, suprapartides can comprise between about 3 and 10 µg of therapeutic payload. In another example, suprapartides can comprise between about 4 and 10 µg of therapeutic payload. In another example, suprapartides can comprise between about 5 and 10 µg of therapeutic payload. In another example, suprapartides can comprise between about 6 and 10 µg of therapeutic payload. In another example, suprapartides can comprise between about 8 and 20 µg of therapeutic payload. In another example, suprapartides can comprise between about 8 and 15 µg of therapeutic payload.

For example, suprapartides can comprise between about 6 and 8 µg of therapeutic payload.

In an example, suprapartides according to the present disclosure comprise at least 1.5 µg of neurotrophic factor. In another example, suprapartides comprise at least 2.0 µg of neurotrophic factor.

In another example, suprapartides comprise at least 2.5 µg of neurotrophic factor. In another example, suprapartides comprise at least 3.0 µg of neurotrophic factor. In another example, suprapartides comprise at least 3.5 µg of neurotrophic factor. In another example, suprapartides comprise at least 4.0 µg of neurotrophic factor. In another example, suprapartides comprise at least 5.0 µg of neurotrophic factor. In another example, suprapartides comprise at least 6.0 µg of neurotrophic factor. In another example, suprapartides comprise at least 7.0 µg of neurotrophic factor. In another example, suprapartides comprise at least 8.0 µg of neurotrophic factor. In another example, suprapartides comprise at least 9.0 µg of neurotrophic factor. In another example, suprapartides comprise at least 10 µg of neurotrophic factor. In another example, suprapartides comprise at least 10.5 µg of neurotrophic factor. In another example, suprapartides comprise at least 11 µg of neurotrophic factor. In another example, suprapartides comprise at least 11.5 µg of neurotrophic factor. In another example, suprapartides comprise at least 12 µg of neurotrophic factor. In another example, suprapartides comprise at least 15 µg of neurotrophic factor. In another example, suprapartides comprise at least 20 µg of neurotrophic factor.

For example, suprapartides can comprise at least 6 µg of neurotrophic factor. In another example, suprapartides can comprise between about 2.5 and 10 µg of neurotrophic factor. In another example, suprapartides can comprise between about 5 and 10 µg of neurotrophic factor. In another example, suprapartides can comprise between about 6 and 10 µg of neurotrophic factor. For example, suprapartides can comprise between about 6 and 8 µg of neurotrophic factor. In another example, suprapartides can comprise between about 8 and 20 µg of neurotrophic factor. In another example, suprapartides can comprise between about 8 and 15 µg of neurotrophic factor.

In an example, suprapartides according to the present disclosure comprise at least 1.5 µg of neurotrophin. In another example, suprapartides comprise at least 2.0 µg of neurotrophin.

In another example, suprapartides comprise at least 2.5 µg of neurotrophin. In another example, suprapartides comprise at least 3.0 µg of neurotrophin. In another example, suprapartides comprise at least 3.5 µg of neurotrophin. In another example, suprapartides comprise at least 4.0 µg of neurotrophin. In another example, suprapartides comprise at least 5.0 µg of neurotrophin. In another example, suprapartides comprise at least 6.0 µg of neurotrophin. In another example, suprapartides comprise at least 7.0 µg of neurotrophin. In another example, suprapartides comprise at least 8.0 µg of neurotrophin. In another example, suprapartides comprise at least 9.0 µg of neurotrophin. In another example, suprapartides comprise at least 10 µg of neurotrophin. In another example, suprapartides comprise at least 10.5 µg of neurotrophin. In another example, suprapartides comprise at least 11 µg of neurotrophin. In another example, suprapartides comprise at least 11.5 µg of neurotrophin. In another example, suprapartides comprise at least 12 µg of neurotrophin. In another example, suprapartides comprise at least 15 µg of neurotrophin. In another example, suprapartides comprise at least 20 µg of neurotrophin.

For example, suprapartides can comprise at least 6 µg of neurotrophin. In another example, suprapartides can comprise between about 2.5 and 10 µg of neurotrophin. In another example, suprapartides can comprise between about 5 and 10 µg of neurotrophin. In another example, suprapartides can comprise between about 6 and 10 µg of neurotrophin. For example, supraparticles can comprise between about 6 and 8 μg of neurotrophin. In another example, supraparticles can comprise between about 8 and 20 μg of neurotrophin. In another example, supraparticles can comprise between about 8 and 15 μg of neurotrophin.

In an example, supraparticles according to the present disclosure comprise at least 1.5 μg of therapeutic payload, wherein the therapeutic payload has an isoelectric point between 9 and 10. In another example, supraparticles comprise at least 2.0 μg of therapeutic payload, wherein the therapeutic payload has an isoelectric point between 9 and 10.

In another example, supraparticles comprise at least 2.5 μg of therapeutic payload, wherein the therapeutic payload has an isoelectric point between 9 and 10. In another example, supraparticles comprise at least 3.0 μg of therapeutic payload, wherein the therapeutic payload has an isoelectric point between 9 and 10. In another example, supraparticles comprise at least 3.5 μg of therapeutic payload, wherein the therapeutic payload has an isoelectric point between 9 and 10. In another example, supraparticles comprise at least 4.0 μg of therapeutic payload, wherein the therapeutic payload has an isoelectric point between 9 and 10. In another example, supraparticles comprise at least 5.0 μg of therapeutic payload, wherein the therapeutic payload has an isoelectric point between 9 and 10. In another example, supraparticles comprise at least 6.0 μg of therapeutic payload, wherein the therapeutic payload has an isoelectric point between 9 and 10. In another example, supraparticles comprise at least 7.0 μg of therapeutic payload, wherein the therapeutic payload has an isoelectric point between 9 and 10. In another example, supraparticles comprise at least 8.0 μg of therapeutic payload, wherein the therapeutic payload has an isoelectric point between 9 and 10. In another example, supraparticles comprise at least 9.0 μg of therapeutic payload, wherein the therapeutic payload has an isoelectric point between 9 and 10. In another example, supraparticles comprise at least 10 μg of therapeutic payload, wherein the therapeutic payload has an isoelectric point between 9 and 10. In another example, supraparticles comprise at least 10.5 μg of therapeutic payload, wherein the therapeutic payload has an isoelectric point between 9 and 10. In another example, supraparticles comprise at least 11 μg of therapeutic payload, wherein the therapeutic payload has an isoelectric point between 9 and 10. In another example, supraparticles comprise at least 11.5 μg of therapeutic payload, wherein the therapeutic payload has an isoelectric point between 9 and 10. In another example, supraparticles comprise at least 12 μg of therapeutic payload, wherein the therapeutic payload has an isoelectric point between 9 and 10. In another example, supraparticles comprise at least 15 μg of therapeutic payload, wherein the therapeutic payload has an isoelectric point between 9 and 10. In another example, supraparticles comprise at least 20 μg of therapeutic payload, wherein the therapeutic payload has an isoelectric point between 9 and 10.

For example, supraparticles can comprise at least 6 μg of therapeutic payload, wherein the therapeutic payload has an isoelectric point between 9 and 10. In another example, supraparticles can comprise between about 2.5 and 10 μg of therapeutic payload, wherein the therapeutic payload has an isoelectric point between 9 and 10. In another example, supraparticles can comprise between about 5 and 10 μg of therapeutic payload, wherein the therapeutic payload has an isoelectric point between 9 and 10. In another example, supraparticles can comprise between about 6 and 10 μg of therapeutic payload, wherein the therapeutic payload has an isoelectric point between 9 and 10. For example, supraparticles can comprise between about 6 and 8 μg of therapeutic payload, wherein the therapeutic payload has an isoelectric point between 9 and 10. In another example, supraparticles can comprise between about 8 and 20 μg of therapeutic payload, wherein the therapeutic payload has an isoelectric point between 9 and 10. In another example, supraparticles can comprise between about 8 and 15 μg of therapeutic payload, wherein the therapeutic payload has an isoelectric point between 9 and 10.

Supraparticles of the present disclosure can be loaded with an above exemplified therapeutic payload and can have a pore size selected from the examples discussed below. In an example, supraparticles are microporous. The term "microporous" is used in the context of the present disclosure to refer to particles having a pore size of less than about 2 nm. For example, microporous supraparticles can have a pore size of about 0.5 nm to about 2 nm. In other examples, microporous supraparticles have a pore size of about 1 nm to about 2 nm, about 1.5 nm to about 2 nm. In another example, supraparticles are mesoporous. The term "mesoporous" is used in the context of the present disclosure to refer to particles having pores with diameters between about 2 nm and about 50 nm. For example, mesoporous supraparticles can have a pore size of about 2 nm to about 50 nm. In other examples, mesoporous supraparticles have a pore size of about 2 nm to about 40 nm, about 2 nm to about 30 nm. In another example, supraparticles are macroporous. The term "macroporous" is used in the context of the present disclosure to refer to particles having a pore size of greater than about 50 nm. For example, macroporous supraparticles can have a pore size of about 50 nm to about 500 nm. In other examples, macroporous supraparticles have a pore size of about 50 nm to about 250 nm, about 50 nm to about 150 nm, about 50 nm to about 100 nm.

In an example, supraparticles are comprised of microporous nanoparticles. In an example, supraparticles are comprised of nanoparticles having a pore size of about 0.5 nm to about 2 nm. In other examples, supraparticles are comprised of nanoparticles having a pore size of about 1 nm to about 2 nm, about 1.5 nm to about 2 nm. In another example, supraparticles are comprised of mesoporous nanoparticles. In an example, supraparticles are comprised of nanoparticles having a pore size of about 2 nm to about 50 nm. In other examples, supraparticles are comprised of nanoparticles having a pore size of about 2 nm to about 40 nm, about 2 nm to about 30 nm. In another example, supraparticles are comprised of macroporous nanoparticles. In an example, supraparticles are comprised of nanoparticles having a pore size of about 50 nm to about 95 nm. In other examples, supraparticles are comprised of nanoparticles having a pore size of about 50 nm to about 85 nm, about 50 nm to about 75 nm, about 50 nm to about 65 nm.

In another example, supraparticles are comprised of nanoparticles having a bimodal pore structure. The term "bimodal" is used in the context of the present disclosure to refer to particles comprising multiple pore sizes, generally a smaller pore size and a larger pore size. For example, supraparticles can comprise nanoparticles having mesopores and macropores. In an example, such supraparticles are comprised of nanoparticles having pores ranging from 2 nm to 95 nm. In another example, supraparticles are comprised of bimodal nanoparticles having pores ranging from 10 nm to 95 nm. In another example, supraparticles are comprised of bimodal nanoparticles having pores ranging from 15 nm to 95 nm.

In other examples, supraparticles can comprise pore sizes ranging from 1 nm to 200 nm. In other examples, supraparticles are comprised of bimodal nanoparticles having smaller pore sizes of about 1 nm to about 5 nm and larger pore sizes of about 10 nm to about 50 nm. In another example, supraparticles are comprised of bimodal nanoparticles having smaller pore sizes of about 2 nm to about 4 nm and larger pore sizes of about 15 nm to about 40 nm. In another example, supraparticles are comprised of bimodal nanoparticles having smaller pore sizes of about 2 nm to about 3 nm and larger pore sizes of about 4 nm to about 40 nm. In other examples, supraparticles are comprised of bimodal nanoparticles having smaller pore sizes of about 10 nm to about 50 nm and larger pore sizes of about 70 nm to about 95 nm. In another example, supraparticles are comprised of bimodal nanoparticles having smaller pore sizes of about 15 nm to about 40 nm and larger pore sizes of about 80 nm to about 95 nm.

In an example, supraparticles are comprised of microparticles. In another example, supraparticles are comprised of microporous microparticles. In an example, supraparticles are comprised of microparticles having a pore size of about 0.5 nm to about 2 nm. In other examples, supraparticles are comprised of microparticles having a pore size of about 1 nm to about 2 nm, about 1.5 nm to about 2 nm. In another example, supraparticles are comprised of mesoporous microparticles. In an example, supraparticles are comprised of microparticles having a pore size of about 2 nm to about 50 nm. In other examples, supraparticles are comprised of microparticles having a pore size of about 2 nm to about 40 nm, about 2 nm to about 30 nm. In another example, supraparticles are comprised of macroporous microparticles. In an example, supraparticles are comprised of microparticles having a pore size of about 50 nm to about 500 nm. In other examples, supraparticles are comprised of microparticles having a pore size of about 50 nm to about 250 nm, about 50 nm to about 150 nm, about 50 nm to about 100 nm.

In another example, supraparticles are comprised of microparticles having a bimodal pore structure. For example, supraparticles can comprise microparticles having mesopores and macropores. In an example, such supraparticles are comprised of microparticles having pores ranging from 2 nm to 500 nm. In another example, supraparticles are comprised of bimodal microparticles having pores ranging from 10 nm to 250 nm. In another example, supraparticles are comprised of bimodal microparticles having pores ranging from 15 nm to 150 nm.

In other examples, supraparticles are comprised of bimodal microparticles having smaller pore sizes of about 1 nm to about 5 nm and larger pore sizes of about 10 nm to about 50 nm. In another example, supraparticles are comprised of bimodal microparticles having smaller pore sizes of about 2 nm to about 4 nm and larger pore sizes of about 15 nm to about 40 nm. In another example, supraparticles are comprised of bimodal microparticles having smaller pore sizes of about 2 nm to about 3 nm and larger pore sizes of about 4 nm to about 40 nm. In other examples, supraparticles are comprised of bimodal microparticles having smaller pore sizes of about 10 nm to about 50 nm and larger pore sizes of about 70 nm to about 200 nm. In another example, supraparticles are comprised of bimodal microparticles having smaller pore sizes of about 15 nm to about 40 nm and larger pore sizes of about 80 nm to about 150 nm. In another example, supraparticles are comprised of bimodal microparticles having smaller pore sizes of about 20 nm to about 30 nm and larger pore sizes of about 100 nm to about 120 nm.

In another example, supraparticles are comprised of microparticles and nanoparticles. In this example, microparticles and nanoparticles can have an above referenced pore size(s). For example, supraparticles can be comprised of microparticles and nanoparticles having a bimodal pore structure.

In an example, supraparticles can have a substantially uniform pore size. In another example, supraparticles comprise variable pore sizes. In this example, pore size may be variable but fall within a particular size range. For example, supraparticles can be predominantly mesoporous. In another example, supraparticles can be predominantly macroporous. In another example, supraparticles are comprised of nanoparticles having a substantially uniform pore size. In another example, supraparticles are comprised of bimodal nanoparticles having substantially uniform small and large pore sizes. In another example, supraparticles are comprised of microparticles having a substantially uniform pore size. In another example, supraparticles are comprised of bimodal microparticles having substantially uniform small and large pore sizes.

In an example, above referenced supraparticles can have an ordered pore structure. These supraparticles have pores with a regular, three-dimensional spacing. In another example, above referenced supraparticles can have a disordered pore structure. These supraparticles have pores with an irregular, three-dimensional spacing. In another example, supraparticles have a combination of both ordered and disordered pore structures.

It will be appreciated by the person skilled in the art that supraparticle pore size can be measured by, for example, transmission electron microscopy (TEM), scanning electron microscopy (SEM) and X-Ray computed tomography. One of skill in the art can identify supraparticles having the above exemplified pore sizes by measuring the width across the widest point of their three dimensional structure. In an example, the widest point or a pore may be at the surface of the supraparticle.

Supraparticles of the present disclosure may be characterised by the distance between their particles. In an example, the average distance between particles can range from about 80 nm to about 400 nm. In another example, the average distance between colloidal particles ranges from about 90 nm to about 300 nm, about 100 nm to In an example, supraparticle pores are connected. For example, supraparticles can comprise a series of interconnected pores. In another example, supraparticle pores are not connected. In another example, supraparticles have a combination of both connected and unconnected pores.

Supraparticles of the present disclosure may be characterised by the volume of their pores. In an example, supraparticle pore volume ranges from about 0.5 mLg$^{-1}$ to about 10 mLg$^{-1}$. In another example, supraparticles have a pore volume of about 0.8 mLg$^{-1}$ to about 5 mLg$^{-1}$, about 1 mLg$^{-1}$ to about 2.5 mLg$^{-1}$, about 1.5 mLg$^{-1}$ to about 2 mLg$^{-1}$.

Supraparticles of the present disclosure may have a hollow core or a toroidal core. In an example, the internal volume of the supraparticle core is at least about 45%, at least about 55%, at least about 65%, at least about 70%, at least about 75%, at least about 80%, at least about 85%, at least about 90%, at least about 95% of the total volume of the supraparticle. Exemplary methods of producing hollow core supraparticles include acid core processes such as those described in U.S. Pat. No. 4,468,498 and ester core process such as those described in U.S. Pat. Nos. 5,157,084 and 5,521,253.

Supraparticles of the present disclosure may be characterised by the surface area of their structure. In an example, the surface area of supraparticles range from about 500 $m^2g^{-1}$ to about 1500 $m^2g^{-1}$. In another example, supraparticles have a surface area of between about 700 $m^2g^{-1}$ and about 1250 $m^2g^{-1}$, about 750 $m^2g^{-1}$ and 1000 $m^2g^{-1}$, about 800 $m^2g^{-1}$ and 900 $m^2g^{-1}$.

In an example, supraparticles of the present disclosure are produced from nanoparticles having a diameter of between about 1 nm and 100 nm. In another example, supraparticles are produced from microparticles having a diameter of between about 0.1 μm and 100 μm. In another example, supraparticles are produced from nanoparticles and microparticles.

Exemplary particles forming the supraparticles of the present disclosure include organic particles, inorganic particles, metal particles or a combination thereof. Exemplary organic particles include polymeric particles such as polyglycolic acid (PGA), polylactic acid (PLA), poly(methacryclic acid), poly(ethacrylic acid), polyacrylic acid (PAA), poly(N-isopropylacrylamide), poly(N,N-dimethylacrylamide), polyamides, poly-2-hydroxy butyrate (PHB), gelatines, polycaprolactone (PCL), and poly (lactic-co-glycolic acid) (PLGA). Exemplary inorganic particles include mineral fillers such as heavy fillers or high density fillers, pigments, clays and other synthetic particles. Other exemplary inorganic particles include dense minerals such as barite, hematite, magnesium oxide, inorganic oxides including titanium dioxide, calcium oxide, zinc oxide, magnesium oxide, cerium oxide, zirconium dioxide, and silicon dioxide. In an example, the material is silicon dioxide (i.e. silica). Thus, in an example, the supraparticles can be referred to as silica supraparticles. Exemplary metal particles include gold, silver, and copper. In one example, supraparticles may comprise the same particles. For example, supraparticles can substantially consist of silica particles. In another example, supraparticles may comprise different particles; for example silica and clay particles. In other examples, supraparticles can comprise at least three, at least four, at least 5, at least 6, at least 7, at least 8, at least 9, at least 10 different particles.

In an example, supraparticles comprise polyelectrolytes or polyelectrolyte material. Examples of such supraparticles are disclosed in WO 2006/037160. In this example, the polyelectrolyte may be a positively charged polyelectrolyte (or have the ability to be positively charged) or a negatively charged polyelectrolyte (or have the ability to be negatively charged) or have a zero net charge.

Supraparticles of the present disclosure can have various shapes. For example, supraparticles can have a spherical shape. Exemplary spherical shapes include spheres and ovoids. In another example, supraparticles have a non-spherical shape. Exemplary non-spherical shapes include dumbbell, hemisphere, disc, tetrahedron, fibre, spherocylinder and irregular shapes. In an example, supraparticles can have an ordered structure. For example, supraparticles may comprise an ordered array.

Spherical supraparticles of the present disclosure may be characterised by their diameter. For example, supraparticles of the present disclosure have a diameter greater than 100 μm. For example, supraparticles of the present disclosure can have a diameter of at least about 150 μm, about 200 μm, about 250 μm, about 300 μm, about 350 μm, about 400 μm, about 450 μm, about 500 μm, about 550 μm, about 600 μm, about 650 p.m, about 700 μm, about 750 μm, about 800 μm, about 850 μm, about 900 μm, about 950 μm, about 1000 μm. In other examples, supraparticles can have a diameter of between about 150 μm and about 1000 μm, about 200 μm and about 900 μm, about 300 μm and about 800 μm. In another example, supraparticles can have a diameter of between about 400 μm and about 600 μm. In another example, supraparticles can have a diameter of between about 450 μm and about 550 μm. In another example, supraparticles can have a diameter of between about 460 μm and about 540 μm. In another example, supraparticles can have a diameter of between about 470 μm and about 530 μm. In another example, supraparticles can have a diameter of between about 480 μm and about 520 μm. In another example, supraparticles can have a diameter of between about 490 μm and about 510 μm. In other examples, supraparticles can be characterised by the width across the widest point of their three dimensional structure. For example, supraparticles can have a width consistent with the above exemplified diameters.

The supraparticles of the present disclosure may also comprise cross linked functional moieties. For example, functional moieties may be crosslinked through a chemical reaction. In an example, polyglycolic acid (PGA) molecules are crosslinked by a chemical reaction of the PGA molecules with cystamine (Tan et al. Adv. Mater. (2012) 24, 3362-3366).

Supraparticles of the present disclosure can be produced using various methods known in the art. Exemplary production methods include wet self-assembly (WSA) and dry self-assembly (DSA) techniques. WSA forms supraparticles by assembly inside or around droplet templates suspended in liquid media. Examples include absorption of particles on two-phase interfaces of emulsion droplets, evaporation of floating particulate suspension droplets and organization of particles with the assistance of microwaves (Park et al. (2006) J. Colloid Interface Sci. 298, 713-719, Kuncicky et al. (2007) Chem Mater. 19, 141-143, Kuncicky et al. (2008) Langmuir. 24, 1371-1380). DSA encompasses methods for fabricating supraparticles using droplet templates dispensed on solid substrates. For example, supraparticles can be produced following particle assembly in droplets residing on superhydrophobic substrates (Rastogi et al. (2008) Adv Mater. 20, 4263-4268). In this example, a particulate suspension of mesoporous silica nanoparticles (about 5 wt %) is applied drop wise to a hydrophilic surface (e.g. paraffin film) before being dried with air flow and annealed at high temperatures (e.g. about 923 K) to form mesoporous silica supraparticles (MS-SPs). In another example, ink jet printing methods can be used to produce supraparticles (Park et al. (2006) J. Colloid Interface Sci. 298, 713-719). Other exemplary supraparticles and methods for their production are described in WO 2001/032760, WO 2006/037160, WO 2009/079688, Wang et al. (2009) J. Mater. Chem. 19, 6451, Wang et al. (2006) Adv. Mater. 18, 795, Wang et al. (2005) Angew. Chem. Int. Ed. 44, 2888. In another example, supraparticles according to the present disclosure are produced by electrospraying. Examples of electrospraying are reviewed in Jaworek A., 2007 Powder Technology 1, 18-35. Examples of electrospraying are also exemplified below. For example, supraparticles can be produced by electrospraying a nanoparticle solution comprising alginic acid. In this example, the supraparticles can be subjected to calcination to remove alginic acid or a derivative thereof at, for example, 650° C.

In another example, the supraparticle surface is modified by the addition of functional moieties to enhance the loading of a therapeutic payload. Any number of functional moieties may be added to the surface of a supraparticle, with the choice of functional moiety being chosen to compliment the therapeutic payload being loaded. In an example, a moiety such as 3-aminopropyltriethoxysilane (APTS), is grafted onto the surface of silica supraparticle. This introduces an amine functionality that can interact with any carboxyl groups present on a therapeutic payload. In another example, the supraparticle is modified to bear an overall net charge that enhances loading of the therapeutic payload (Tan et al. Adv. Mater. (2012) 24, 3362-3366). For example, the surface of the supraparticle can be modified to bear an overall net positive charge, such that loading of a therapeutic payload bearing an overall net negative charge is enhanced. In another example, the surface of the supraparticle is modified to bear an overall net negative charge, such that loading of a therapeutic payload bearing an overall net positive charge is enhanced.

The supraparticles of the present disclosure may also comprise cross linked functional moieties. For example, functional moieties may be crosslinked through a chemical reaction. In an example, polyglycolic acid (PGA) molecules are crosslinked by a chemical reaction of the PGA molecules with cystamine (Tan et al. Adv. Mater. (2012) 24, 3362-3366).

Therapeutic Payload

Supraparticles can deliver therapeutics to the inner ear in sufficient quantities and over a sufficient duration to enhance cell survival in the ear. Supraparticles according to the present disclosure can comprise various therapeutic payloads. The "therapeutic payload" can be any agent useful for treating an auditory disorder. Examples of agents include biological products such as polynucleotides, antibodies, monoclonal antibodies, antibody fragments, antibody drug conjugates, proteins, biologically active proteins, fusion proteins, recombinant proteins, peptides, polypeptides, synthesized polypeptides, vaccines, therapeutic serums, viruses, polynucleotides, cells such as stem cells or parts thereof as well as small molecules.

Exemplary viral therapeutic payloads can comprise appropriately modified retrovirus, Adenovirus (AdV), Adeno-associated virus (AAV) or a recombinant form such as recombinant adeno-associated virus (rAAV) and derivatives thereof such as self-complementary AAV (scAAV) and non-integrating AV. Other exemplary viral therapeutic payloads can comprise herpes simplex virus (HSV), lentivirus, vaccina and vesicular stomatitis virus (VSV). For example, the viral therapeutic payload can comprise AAV. Various AAV serotypes are known an may be suitable viral payloads. In an example, the AAV is serotype 2. In another example, the AAV is serotype 1. In other examples, the AAV is serotype 3, 4, 7, 8, 9, 10, 11, 12 or 13.

In an example, the small molecule may be a neurotransmitter. The term "neurotransmitter" is used in the context of the present disclosure to refer to a substance that transmits signal(s) across a chemical synapse from one cell to another. Generally, a neurotransmitter transmits signal(s) across a chemical synapse from one neuron to a target cell such as another neuron, muscle cell or gland cell. In another example, the small molecule is a receptor agonist. The term "agonist" is used in the context of the present disclosure to refer to a substance which initiates a physiological response when combined with a receptor. In another example, the small molecule is a receptor antagonist. The term "antagonist" is used in the context of the present disclosure to refer to a substance which interferes with or inhibits the physiological action of a receptor.

Exemplary polynucleotides include antisense polynucleotides, double stranded DNA (dsDNA) or double stranded RNA (dsRNA). In one example, the dsDNA or dsRNA is an aptamer. In another example, the dsRNA is a siRNA, miRNA or shRNA.

Exemplary antibodies and fragments thereof include human antibodies, humanized antibodies, chimeric antibodies, single chain antibodies, diabodies, triabodies, tetrabodies or single domain antibodies. In an example, the antibody can be bi-specific, an antibody-drug conjugate or a biosimilar antibody. Other exemplary polypeptides include cytokines, chemokines, hormones and blood coagulation factors. In an example the polypeptide is an enzyme. Exemplary enzymes include proteases, lipases, asparaginases, liprotamases, tissue plasminogen activators, collagenases, glutaminases, hyaluronidases, streptokinases, uricases, urokinases or nucleases, such as a programmable nuclease. In an example, the enzyme can be a programmable nuclease targeted to introduce a genetic modification into a gene or a regulator region thereof. For example, the programmable nuclease can be a RNA-guided engineered nuclease (RGEN). In an example, the RGEN is from an archaeal genome or may be a recombinant version thereof. In another example, the RGEN may be from a bacterial genome or is a recombinant version thereof. In another example, the RGEN is from a Type I (CRISPR)-cas (CRISPR-associated) system. In another example, the RGEN is from a Type II (CRISPR)-cas (CRISPR-associated) system. In another example, the RGEN is from a Type III (CRISPR)-cas (CRISPR-associated) system. In an example, the nuclease is from a class I RGEN or a class II RGEN.

In another example, the therapeutic payload may be an antigen which stimulates an immune response in a subject. Exemplary antigens include proteins, peptides, polysaccharides or oligosaccharides (free or conjugated to a protein carrier) or mixtures thereof. Other exemplary antigens include cells or parts thereof or a viral particle or a part thereof.

In an example, the therapeutic payload is useful for treating one or more neurological disorders, such as Alzheimer's disease, Parkinson's disease, Epilepsy or multiple sclerosis.

In an example, the payload is a "neurotrophic factor". The term neurotrophic factor is used in the context of the present disclosure to refer to molecules that enhance the growth or survival potential of any cells including those from the auditory system including auditory neurons and/or their synaptic connections. For example, neurotrophic factors encompassed by the present disclosure can enhance growth or survival of cells from the auditory system located in the middle ear, inner ear or vestibular system. Examples of these cells are discussed above.

Exemplary neurotrophic factors can include agents discussed above with known therapeutic efficacy for directly or indirectly enhancing survival of cells from the auditory system and/or their synaptic connections.

In an example, the neurotrophic factor is a neurotrophic peptide. Exemplary neurotrophic peptides include, brain derived neurotrophic factor (BDNF), nerve growth factor, neurotrophin-3, neurotrophin-4, members of the ciliary neurotrophic factor (CNTF) family such as CNTF, Leukemia inhibitory factor (LIF), Interleukin-6 (IL-6), Glia maturation factor (GMF), insulin growth factor-1 (IGF-1), Neuregulin 1, Neuregulin 2, Neuregulin 3 and Neuregulin 4, vascular endothelial growth factor (VEGF), members of the Glial Cell Derived Neurotrophic Factor (GDNF) family such as GDNF, neurturin (NRTN), artemin (ARTN), and persephin (PSPN), ephrins such as A1, A2, A3, A4, A5, B1, B2 and B3, insulin growth factor-1 (IGF-1) and interleukins such as IL-11.

One cause of spiral ganglion neuron degeneration is the loss of the endogenous supply of neurotrophins. Thus, in an example, the neurotrophic factor is a 20 neurotrophin. The term "neurotrophin" is used in the context of the present disclosure to refer to proteins that induce the survival, development and/or function of neurons and/or their synaptic connections. Exemplary neurotrophins are discussed above and include BDNF, nerve growth factor, neurotrophin-3 and neurotrophin-4. Accordingly, in an example, the supraparticle comprises BDNF. In another example, the supraparticle comprises nerve growth factor. In another example, the supraparticle comprises neurotrophin-3. In another example, the supraparticle comprises neurotrophin-4. In an example, supraparticles can comprise at least two different neurotrophins. In other examples, supraparticles can comprise at least three or four different neurotrophins. In an example, the supraparticle does not comprise BDNF.

Therapeutic efficacy may be improved by administering supraparticles comprising multiple different therapeutic payloads. Thus, in an example, supraparticles can comprise at least two, at least three, at least four, at least five, at least six, at least seven, at least eight, at least nine, at least 10 different therapeutic payloads.

For example, supraparticles can comprise at least two different neurotrophic factors. In other examples, supraparticles can comprise at least three, at least four, at least five different neuroptrophic factors. In these examples, various combinations of neurotrophic factors such as neurotrophins are contemplated. Exemplary combinations of neurotrophic factors include BDNF and nerve growth factor, BDNF and neurotrophin-3, BDNF and neurotrophin-4, BDNF and CNTF, BDNF and GDNF, BDNF and IL-11, neurotrophin-3 and neurotrophin-4, neurotrophin-3 and CNTF, neurotrophin-3 and CNTF, neurotrophin-3 and GDNF, neurotrophin-3 and IL-11, neurotrophin-4 and CNTF, neurotrophin-4 and GDNF, neurotrophin-4 and IL-11, CNTF and GDNF, CNTF and IL-11, GDNF and IL-11, BDNF, neurotrophin-3 and neurotrophin-4, BDNF, neurotrophin-3 and CNTF, BDNF, neurotrophin-3 and GDNF, BDNF, CNTF and GDNF, BDNF, CNTF and IL-11, neurotrophin-3, neurotrophin-4 and CNTF, neurotrophin-3, neurotrophin-4 and GDNF, neurotrophin-3, CDNF and GDNF, neurotrophin-3, neurotrophin-4 and IL-11, neurotrophin-4, CNTF and GDNF, neurotrophin-4, CNTF and IL-11, BDNF, neurotrophin-3, neurotrophin-4 and CNTF, BDNF, neurotrophin-3, neurotrophin-4 and GDNF, BDNF, neurotrophin-3, CNTF and GDNF, BDNF, neurotrophin-4, CNTF and GDNF, BDNF, BDNF, neurotrophin-3, neurotrophin-4 and IL-11, neurotrophin-3, neurotrophin-4, CNTF and GDNF, neurotrophin-3, neurotrophin-4, CNTF and IL-11.

Various otological interventions such as surgical procedures and implantation of hearing devices can result in side effects such as tissue damage, inflammation and/or infection in the middle and inner ear. Biological response(s) mounted against such side effects can indirectly affect the growth or survival potential of cells from the auditory system and/or their synaptic connections. Thus, in an example, neurotrophic factors assist in tissue repair, reducing inflammation and/or reducing infection. Accordingly, additional exemplary neurotrophic factors include steroids or antioxidants. Other exemplary neurotrophic factors include antibodies or other binding proteins such as anti-Tropomyosin receptor kinase (TrK) B, anti-TrK C or binding proteins that interact with p75 neurotrophin receptor. For example, p75 neurotrophin receptor antagonists. In another example, neurotrophic factors include nucleic acids. For example, the neurotrophic factor can comprise a gene therapy, silencing RNA such as a siRNA or miRNA, expression constructs such as DNA plasmids comprising a nucleic acid of interest. In an example, the neurotrophic factor is an expression construct comprising a nucleic acid encoding an opsin(s).

Additional exemplary combinations of neurotrophic factors include a steroid, an antioxidant, an antibody or a nucleic acid and at least one, at least two, at least three, at least four, at least five different neurotrophic factor(s). For example, a supraparticle can comprise a steroid such as dexamethasone and any one or more of BDNF, nerve growth factor, neurotrophin-3, neurotrophin-4, GDNF and IL-11. In another example, a supraparticle can comprise an expression vector comprising an opsin and any one or more of BDNF, nerve growth factor, neurotrophin-3, neurotrophin-4 and GDNF. In another example, a supraparticle can comprise an antibody such as anti-Tropomyosin receptor kinase (TrK) B or anti-TrK C and any one or more of BDNF, nerve growth factor, neurotrophin-3, neurotrophin-4 and GDNF.

In an example, supraparticles can comprise at least two, at least three, at least four, at least five different therapeutic payloads wherein at least one therapeutic payload is a neurotrophic factor. For example, supraparticles can comprise at least three different therapeutic payloads wherein two therapeutic payloads are neurotrophic factors. In another example, supraparticles can comprise at least four different therapeutic payloads wherein three therapeutic payloads are neurotrophic factors. In these examples, the therapeutic payload need not enhance the growth or survival potential of cells from the auditory system but rather can provide another therapeutic benefit. For example, the therapeutic payload may suppress a subject's immune system following administration of supraparticles. In another example, supraparticles may comprise a payload that reduces survival of cells from the auditory system or their synaptic connections and a neurotropic factor(s). In this example, the neurotrophic factor may alleviate the reduction in survival of cells from the auditory system or their synaptic connections. In an example, supraparticles comprise antineoplastic agents including cisplatinum or related compounds, antibiotics including aminoglycosides such as tobrahmycin or related compounds, loop diuretics such as furosemide, antimetabolites such as methotrexate, salicylates such as aspirin or a radioactive moiety and a neurotrophic factor(s). For example, a supraparticle can comprise an antibiotic and any one or more of BDNF, nerve growth factor, neurotrophin-3, neurotrophin-4, GDNF and IL-11.

Depending on the site of administration the therapeutic payload may need to diffuse from the middle ear to the inner ear or vestibular system. This may occur via diffusion of the therapeutic payload across the round or oval widows. Thus, in an example, supraparticles may comprise a molecule(s) that assist diffusion of the therapeutic payload across the round and oval windows to the inner ear and/or vestibular system.

In an example, the therapeutic payload has an isoelectric point greater than 7. In another example, the therapeutic payload has an isoelectric point greater than 8. In another example, the therapeutic payload has an isoelectric point greater than 9. In another example, the therapeutic payload has an isoelectric point greater than 10. In another example, the therapeutic payload has an isoelectric point between 7 and 10. In another example, the therapeutic payload has an isoelectric point between 7 and 9. In another example, the therapeutic payload has an isoelectric point between 8 and 10. In another example, the therapeutic payload has an isoelectric point between 9 and 10.

Various methods of producing a supraparticles comprising a therapeutic payload(s) are known in the art. Supraparticles comprising a therapeutic payload may be referred to loaded supraparticles in the context of the present disclosure. Methods of producing loaded supraparticles are not particularly limited so long as the resulting supraparticle can carry the therapeutic payload to the ear of a subject. Exemplary methods of loading are reviewed in Wang et al. (2009) J. Mater. Chem. 19, 6451 and include therapeutic payload encapsulation and entrapment. In one example, supraparticles may be loaded by contacting the supraparticle with an aqueous solution of the therapeutic payload followed by a period of incubation. The therapeutic payload solution can contain an excess of the amount of therapeutic payload to be loaded onto the supraparticle and incubation can occur at room temperature. Agitation of the solution containing the supraparticle and the therapeutic payload may be used to enhance loading of the payload.

One of skill in the art will appreciate that the required level of therapeutic payload will likely be influenced by the therapeutic payload itself and the indication being treated according to the present disclosure.

Formulations

Supraparticles may be formulated as a pharmaceutical composition suitable for administration to a subject. Exemplary pharmaceutical compositions may provide supraparticles alone or in combination with a pharmaceutically acceptable carrier, diluent or excipient. In these compositions supraparticles are provided in an amount sufficient to deliver a therapeutically effective amount of therapeutic payload to the ear of a subject. Depending upon the particular route of administration, a variety of acceptable carriers, known in the art may be used, as for example described in Remington's Pharmaceutical Sciences (Mack Publishing Co. N.J. USA, 1991).

Exemplary pharmaceutical compositions may also comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils, and injectable organic esters such as ethyl oleate. Proper fluidity can be maintained, for example, by the use of coating materials such as lecithin, by the maintenance of the required particle size in the case of dispersions, and by the use of surfactants. Such compositions may also contain adjuvants such as preservatives, wetting agents, emulsifying agents, and dispersing agents or antibacterial and antifungal agents.

In another example, supraparticles can be incorporated into slow release or targeted delivery systems. Such slow release systems can include foams, gels, drops and sprays for topical administration or a depot for injection. Exemplary slow release systems include polymer matrices, liposomes, and microspheres. Polymer matrices include reservoir based systems where supraparticles are enclosed in porous polymer coatings (Yang and Pierstorff (2012) JALA. 17, 50-58) and monolithic matrix systems where supraparticles are embedded in polymer matrices (Langer R (1990) Science. 249, 1527-1533). Liposomes may be biodegradable and amphiphilic drug delivery systems, which may be formulated using phospholipids and cholesterol. Microspheres may be formulated using biodegradable and biocompatible polymers.

In another example, supraparticles are provided in a formulation that enhances diffusion across a membrane within the subjects ear such as the tympanic membrane, oval or round windows. For example, supraparticle formulations may comprise artificial perilymph.

Combination Therapy

The supraparticle of the present disclosure can be combined with other therapeutic intervention to improve treatment. For example, supraparticles may be administered in combination with a hearing aid. In another example, supraparticles may be administered in combination with one or more additional drug(s) that are useful for the treatment of the auditory disorder, hearing loss or an associated pathology such as inflammation or infection. In an example, additional drug(s) may be administered in the same formulation as the supraparticle. In another example, additional drug(s) may be administered in a separate formulation. In this example, supraparticles may be administered sequentially or simultaneously with the other drug(s). Further, the additional drug(s) may be administered via an alternative route to the supraparticle such as systemically, intramuscularly or orally.

Various otic interventions result in the cochlea being directly accessible and thus provide the opportunity of implanting supraparticles inside the cochlea. Accordingly, supraparticles of the present disclosure may be administered in combination with otic intervention in order to treat an auditory disorder, enhance the growth or survival potential of cells from the auditory system and/or to protect residual hearing.

Exemplary otic interventions encompassed by the present disclosure include implants and otic surgery. Exemplary implants include auris-interna or auris-media medical devices such as cochlear devices, hearing sparing devices, hearing-improvement devices, tympanostomy tubes, short electrodes, micro-prostheses or piston-like prostheses, needles, stem cell transplants, drug delivery devices. Exemplary otic surgeries include inner ear surgery, tympanostomy, cochleostomy, labyrinthotomy, mastoidectomy, stapedectomy, stapedotomy, endolymphatic sacculotomy or the like.

Accordingly, in an example, the methods of the present disclosure encompass, administering a supraparticle and implanting a cochlear device. In an example, the cochlea device is provided with a tunnel through to the inner ear. Such a tunnel can facilitate provision of multiple doses of supraparticles to the inner ear over time. In these example, Supraparticles may promote peripheral regrowth of the nerve fibres to be in closer proximity to the electrodes of the cochlear device.

Administration

The present disclosure also encompasses methods of delivering a therapeutic payload to a cell, tissue or organ in a subject via the ear, the method comprising administering to the ear of a subject a supraparticle according to the present disclosure.

In an example, the method delivers a therapeutic payload to a cell from the subjects inner ear, middle ear and/or vestibular system. In another example, the method delivers a therapeutic payload to a neural cell, neural tissue or the brain.

In an example, supraparticles may be attached to a cochlear electrode array prior to implantation. Accordingly, in an example, the methods of the present disclosure encompass a method of treating hearing loss comprising implanting a cochlear electrode array comprising supraparticles according to the present disclosure.

Compositions according to the present disclosure are administered to one or both ears of a subject. As used herein, the "subject" can be any organism with an auditory disorder. In an example, the subject is a mammal. In one example, the subject is a human. For example, the human subject can be an adult. In an example, the human subject is a child. Other exemplary mammalian subjects include companion animals such as dogs or cats, or livestock animals such as horses or cows. Terms such as "subject", "patient" or "individual" are terms that can, in context, be used interchangeably in the present disclosure. Subjects treated according to the present disclosure may have hearing loss clinically described as mild, moderate, severe or profound. In an example, subjects have mild hearing loss. In another example, subjects have moderate hearing loss. In another example, subjects have severe hearing loss. In another example, subjects have profound hearing loss or are clinically described as deaf.

Treatment may be restricted to subjects with poor hearing. Such subjects may include those that can not achieve an acceptable level of hearing with the assistance of a hearing aid. Thus, in an example, subjects treated according to the present disclosure can have hearing loss clinically described as moderate, severe or profound. In another example, subjects have severe or profound hearing loss.

In an example, compositions are administered onto the tympanic membrane. In this example, compositions may be formulated for topical administration (e.g. drops, gels, foams, sprays).

In another example, compositions are administered to the "middle ear" cavity. The term "middle ear" in the context of the present disclosure is used to refer to the space between the tympanic membrane and the inner ear. Thus, the middle ear is external to all inner ear tissue. For example, compositions can be administered to the middle ear via injection through the tympanic membrane. In this example, supraparticles may be administered as a depot injection. In another example, an opening in the tympanic membrane can be produced by a treating clinician to facilitate access of compositions to the middle ear. When administering compositions to the middle ear, compositions can be administered onto the round and/or oval window.

In another example, supraparticles are administered into the inner ear. For example, supraparticles can be administered to the cochlea. In an example, supraparticles can be administered to the basal turn of the cochlea. Surgical techniques to gain access to the cochlea or other structures of the inner ear are known in the art. Exemplary techniques for surgically accessing the human cochlea are described in, for example, Clark GM, et al., "Surgery for an improved multiple-channel cochlear implant", Ann Otol Rhinol Laryngol 93:204-7, 1984, and in Clark GM, et al., "Surgical and safety considerations of multichannel cochlear implants in children", Ear and Hearing Suppl. 12:15S-24S, 1991.

Combination of supraparticles with otic intervention is discussed above. In these examples, otic intervention may occur simultaneously with administration of supraparticles. For example, a cochlear device can be implanted simultaneously with supraparticles. However, increased survival of spiral ganglion neurons can improve the utility of a cochlear implant. Thus, it may be desirable to implant a cochlear device after supraparticles have been administered. For example, a cochlear device can be implanted about one month, about two months, about three months, about six months after the supraparticles have been administered. In these examples, additional supraparticles can be administered with the cochlear device.

In an example, a therapeutically effective amount is administered to the subject. In an example, multiple supraparticles are administered. For example, at least two, at least three, at least four, at least 5, at least 10, at least 20 supraparticles can be administered to an ear of the subject. In another example, about one to 10 supraparticles are administered. In other examples about two to 9, about three to 8, about four to 7, about 5 to 6 supraparticles are administered to an ear of the subject. In these examples, supraparticles can comprise the same payload. Alternatively, in another example, supraparticles are loaded with different payloads. For example, a supraparticle loaded with a neurotrophic factor and a supraparticle loaded with a steroid may be administered. In another example, a supraparticle loaded with a neurotrophic factor and a supraparticle loaded with an antibiotic may be administered. In another example, a supraparticle loaded with a neurotrophic factor can be administered with an antibiotic.

One of skill in the art will appreciate that symptoms of auditory disorders such as hearing loss can vary between ears. For example, hearing loss in one ear may be more severe one ear of a subject when compared to the other ear. Thus, in an example, administered dose may be varied between ears as required.

Compositions/Kits

Supraparticles according to the present disclosure can be provided in a kit or pack. For example, compositions disclosed herein may be packaged in a suitable container with written instructions for treating an auditory disorder. In an example, compositions may be provided in a single dose container such as an ear dropper or pre-filled syringe.

In one example, the kit comprises a supraparticle according to the present disclosure for use in methods of treating an auditory disorder. In another example, the kit comprises a supraparticle according to the present disclosure for use in methods of treating hearing loss. In these examples, the kit may further comprise a hearing aid or an implant such as those discussed above. Accordingly, in an example, the kit can comprise a supraparticle and a cochlear implant.

EXAMPLES

Example 1

Materials and Methods

Experimental Animals

Seven young adult pigmented guinea pigs of either sex (mean 550 g) were used in this study. All procedures were approved by the appropriate ethics committee in accordance with the National Institutes of Health (NIH) Guidelines for the Care and Use of Laboratory Animals, and conformed to the Code of Practice of the National Health and Medical Research Council of Australia.

Auditory Brainstem Responses

Only animals with otoscopically normal external ears were used in this study. Prior to any surgical procedure the hearing status was assessed under anesthesia (ketamine, 60 mg/kg (Parnell Australia) and xylazine, 4 mg/kg (Ilium, Australia); intramuscular injection). Auditory brainstem responses (ABRs) were measured to assess the hearing status of the guinea pigs before and after deafening using procedures described previously (Wise et al. (2005) J Comp Neurol. 487, 147-165; Wise et al. (2010) Mol Ther. 18, 1111-1122). The anaesthetized guinea pigs were placed on a heat pad with the temperature maintained at 37° C. in a sound attenuated room and needle electrodes were placed at the skull vertex, at the nape of the neck and on the abdomen. ABRs were measured to acoustic clicks delivered by a calibrated speaker at intensities up to 100 dB peak equivalent (p.e.) sound pressure level (SPL). The ABR was amplified, recorded to computer and averaged over 200 trials that were presented at stimulus intensities ranging from 0 dB to 100 dB p.e. SPL. Hearing threshold was determined and only guinea pigs with normal hearing thresholds in both ears (ABR threshold <50 dB p.e. SPL) were used in the study.

Toxin Induced Deafening Procedure

Animals were deafened ototoxically using a procedure which has been previously shown to produce a severe bilateral SNHL (Shepherd et al. (2005) J Comp Neurol. 486, 145-158; Wise et al. (2010) Mol Ther. 18, 1111-1122; Landry et al. (2011) Hear Res. 282, 303-313). Under gaseous anesthesia (1-2% isoflurane in 02, 1 L/min) the right jugular vein was exposed and cannulated. Frusemide (130 mg/kg; Ilium, Australia) diluted in warm Hartmann's solution was slowly injected. The vein was tied off and the incision sealed with cyanoacrylate. The ototoxic aminoglycoside kanamycin sulfate (420 mg/kg; Sigma-Aldrich, USA) dissolved in 3 ml Hartmann's solution was then injected subcutaneously (s.c.). Approximately four days after the deafening procedure ABRs were re-measured, using gaseous anaesthetic as described above, to confirm deafness. An increase in hearing thresholds of >50 dB indicated severe to profound SNHL. All thresholds recorded were >100 dB p.e. SPL, which was the maximum intensity presented.

Supraparticle Preparation

Mesoporous silica (MS) nanoparticles, were prepared according to Wang et al. (2010) Chem Mater. 22, 3829-3831. MS nanoparticles were dispersed in Milli-Q water with a particle concentration of 5 wt % and briefly sonicated to form a stable colloidal suspension. A 0.5 to 2.0 µL aliquot of the MS nanoparticle dispersion was then applied to a flat surface, which was pre-covered with a paraffin film. The droplets were dried under air flow to drive assembly of the MS nanoparticles into mesoporous silica suprapaticles (MS-SPs) via capillary force action. The size of the MS-SPs was controlled by the volume of the nanoparticle dispersion applied in the droplet.

Under capillary force, the MS colloids self-assemble into a compact structure to form MS-SPs. The MS-SPs were then removed from the paraffin film and transferred into a ceramic container, and annealed at 923 K to enhance mechanical stability of the MS-SPs. The MS-SPs were collected, and were shown to have a bimodal pore structure (2-3 nm and 15-30 nm) and the macropores within the MS-SP, the space between the densely packed nanoparticles, was 100-200 nm, resulting in a porous structure with a high surface area. The MS-SPs used in this study had a diameter of ca. 580 µm.

Supraparticle Sterilization, Neurotrophin Loading and Neurotrophin Release Properties MS-SPs were sterilized by soaking them in 100 µl of ethanol (80 vol/vol %) for 4 hours prior to rinsing with 100 µl of Milli-Q water six times. MS-SPs were then washed once in 0.1 M phosphate buffered saline (PBS). Eight MS-SPs were loaded for each experimental animal by placing them in an Eppendorf tube containing 15 µl of BDNF (Geneway, BDNF Human Protein, Cat. #10-663-45078) solution (1 mg/ml of BDNF) and incubating them at ambient room temperature for three days with occasional hand shaking.

Immediately prior to implantation the BDNF-loaded MS-SPs (BDNF-MS-SPs) were rinsed once in 20 µl of Milli-Q water. The MS-SPs possess large pore volumes and high surface areas, and therefore allow loading of large amounts of BDNF at therapeutically relevant concentrations required for effective nerve survival in the cochlea.

Bilateral Implant Surgery

One week following deafening the animals underwent bilateral cochlear implant surgery using aseptic surgical techniques. Guinea pigs were anaesthetized with an intramuscular injection of ketamine (60 mg per kg body weight) and xylazine (4 mg per kg body weight). Using a post-auricular approach, the bulla was exposed and a small hole was drilled to expose the basal turn of the cochlea. A cochleostomy (approximately 800 gm) was made using a 0.8 mm diamond drill and gentle suction was applied to remove bone debris from the cochlea (FIGS. 1A-1B). SPs were suspended in sterile saline and 8 SPs were placed into the basal turn of the cochlea using a 21 gauge polyurethane catheter (Optiva, Medex Medical, UK). One cochlea was implanted with BDNF-SPs and the other cochlea was implanted with unloaded SPs (control-SPs) using identical surgical techniques. The side implanted with the BDNF-SPs was randomized. Following implantation, a small piece of muscle was placed over the cochleostomy in order to seal the cochlea. The wound was closed by suturing surrounding muscles in two layers and closing the skin incision with staples. Hartmann's solution (10 ml/kg; s.c.), the antibiotic Baytril (Bayer, Germany) (0.10 mg/kg; s.c.), and the analgesic Temgesic (Reckitt-Benckiser, UK) (50 mg/kg; s.c.) were given after surgery and on the next day to aid recovery.

Tissue Collection and Preparation

Following the 28 day treatment period, the animals were given an overdose of pentobarbital (150 mg/kg; intraperitoneal) and transcardially perfused with 0.9% NaCl (37° C.) followed by 10% Neutral Buffered Formalin (10% NBF; 4° C.). The cochleae were dissected and a small hole was made in the apex. The round and oval windows were incised with a 25 gauge needle and the cochleae post-fixed in 10% NBF for one hour on a shaker at room temperature. The cochleae were then placed in 10% ethylenediamine tetraacetic acid (EDTA) in PBS at room temperature for decalcification. After decalcification, cochleae were cryo-protected in 15% and then 30% sucrose solution before they were embedded in Tissue-Tek O.C.T. cryosectioning compound (Sakura, Japan) as described previously (Landry et al. (2011) Hear Res. 282, 303-313) and stored at −80° C. Cochleae were sectioned at 12 gm using a CM 1900 UV cryostat (Leica, Germany) at −22° C. in the modiolar plane and mounted onto Superfrost-Plus slides (Menzel-Glaser, Braunschweig, Germany). A representative series of cochlear sections were stained with Mayer's haemotoxylin and Putt's eosin (H&E) for general qualitative examination and SGN density measurements within Rosenthal's canal.

Spiral Ganglion Neuron Density Measurement

All quantification was carried out by a single observer blinded to the experimental groups. Sections were viewed and imaged using an Axio Lab microscope and software (Zeiss, Germany). The area of Rosenthal's canal was measured for each cochlear region (Region 1 to 8; see FIGS. 1A-1B) using ImageJ V1.46 (NTH, USA, http COLON SLASH SLASH rsb.info.nih.gov/ij/index.html). SGNs were identified within Rosenthal's canal and counted. Only SGNs exhibiting a clear nucleus were counted using previously published techniques (Wise et al. (2011) Neurotherapeutics. 8, 774-787). Data was collected from five non-continuous sections with a separation of 72 µm ensuring that no cell was counted more than once. The density of the SGNs was determined for each cochlear region as an average from five sections. In the apical cochlear regions (regions 6-8) Rosenthal's canal typically narrows and therefore SGN density data for regions 6-8 were combined.

Tissue Response Measurements

In order to quantify the immune response to the implanted SPs, the extent of fibrosis and new bone growth in the cochlea was measured in hematoxylin and eosin-stained sections at three different locations separated by a distance of at least 400 µm. The tissue response was quantified as the percentage of the area of the scala tympani occupied by any inflammatory cells or tissue growth using techniques previously described (Wise et al. (2011) Neurotherapeutics. 8, 774-787). Briefly, an image of the scala tympani was captured and the area measured. The 'Moments' algorithm in Image J was used to threshold the image to identify the tissue response. The area of scala tympani was measured and the proportion of the scala tympani occupied by the tissue response was calculated. Data was measured from a total of six positions within the cochlea and with three data points per cochleae averaged for the lower basal region (Ai-Aiii) and three data points averaged for the upper basal region (Bi-Biii) (see FIG. 1A).

Statistics

Statistical comparisons of SGN density and tissue response were made by comparing data from the cochleae implanted with BDNF-SPs to the data in the contralateral control cochlea that were implanted with control-SPs. A repeated measures (RM) analysis of variance (ANOVA) using $p<0.05$ level of significance was used to determine statistical significance and post hoc comparisons were made using the Holm Sidak method.

Example 2

Model of Deafness

Deafened animals exhibited ABR thresholds over 100 dB SPL p.e. (data not shown). Histological analysis confirmed that the organ of Corti had completely collapsed, indicating that the deafening procedure resulted in complete loss of hair cells and degeneration of the supporting cells, such that there was typically a completely flattened epithelium (FIGS. 2A-2F). The effects of the deafening technique are symmetrical with SGN loss similar between ears (Xu et al. (1993) Hear Res. 70, 205-215) indicating that the contralateral cochlea serves as a reliable control for experimental techniques designed to improve SGN survival.

Example 3

Spiral Ganglion Neuron Survival

Cochlear sections were examined and quantified to determine the effect of BDNF-SP treatment on SGN survival. FIGS. 2A-2F shows representative examples of cochlear regions 1-5 (R1-5) taken from a cochlea implanted with BDNF-SPs (left panel) and from a control cochlea implanted with Control-SPs (right panel). Aminoglycoside deafening resulted in bilateral threshold shift of >50 dB to acoustic clicks (data not shown) and complete loss of the organ of Corti throughout the cochlea (FIGS. 2A-2F).

SGN survival was observed throughout a wide spatial extent of the cochlea in all but the most apical cochlear regions with SGN densities that were consistent with neural densities in normal hearing guinea pigs from previous studies (Wise et al. (2005) J Comp Neurol. 487, 147-165; Shepherd et al. (2008) Hear Res. 242, 100-109). Of note is that many of the other clinically translatable approaches to deliver neurotrophins to the cochlea such as gene therapy, cell-based therapy, electrode coatings and hydrogels placed on the round window have observed SGN survival effects restricted to the basal cochlear regions, in close proximity to the drug delivery device.

Accordingly, the present results provide direct evidence that a therapeutic level of BDNF was present in the upper middle cochlear regions as demonstrated by improved SGN survival in these regions.

Example 4

Noise Induced Hearing Loss

Figures 3A, 3B:
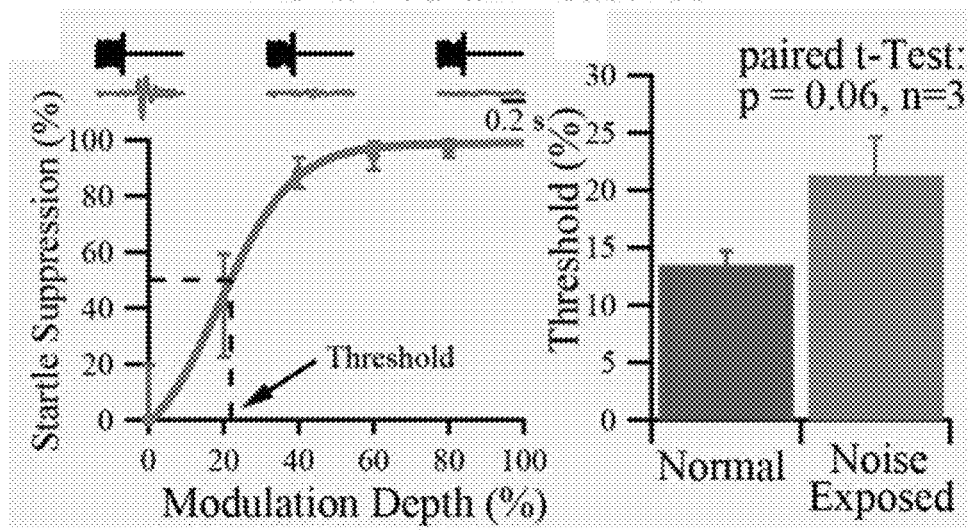
Figures 3C, 3D:
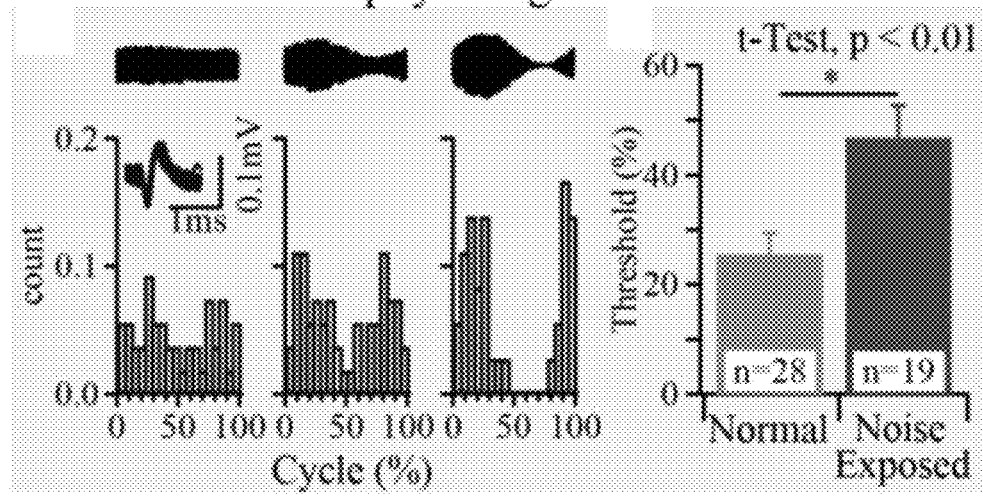

In terms of functional deficits in animal models of synaptopathy, the most commonly reported change is a reduction in the amplitude of evoked auditory responses as a consequence of fewer auditory neurons activated by the acoustic stimulus. However, the data in FIGS. 3A-3C shows for the first time in behavioural experiments, and from neural recordings in the inferior colliculus, that there is a deficit in the detection of modulated acoustic stimuli in animals with cochlear synaptopathy following noise exposure. The perceptual deficits from cochlear synaptopathy are real and measureable using behavioural task and electrophysiological recordings, and importantly, enable assessment of neurotrophin therapy to repair lost synapses.

Damage from noise exposure extends well beyond the epicentre of hair cell loss. The data shows that synaptopathy occurs in the surviving inner hair cells (e.g. FIGS. 4A-4B). Experiments were performed to determine whether intracochlear implantation (FIG. 4B) of supraparticles loaded with neurotrophins could recover lost auditory synapses following damaging noise exposure that caused significant hair cell loss. The outcomes of these experiments were outstanding; complete recovery in synapse numbers was shown following neurotrophin treatment (FIG. 4B).

Example 5

Biocompatibility of Supraparticles

A prerequisite for the clinical viability of the SP drug delivery system is that it is safe for implantation in humans. In order to determine the safety of the SP for drug delivery the tissue response to implantation of BDNF-SPs and Control-SPs was quantified within the cochlea (see FIGS. 1A-1B). Tissue response was quantified by measuring the proportion of the scala tympani occupied by the new tissue and the data is presented in FIGS. 5A-5B.

There was a significant interaction between cochlear Region and SP Treatment (two way repeated measures ANOVA, $p=0.029$). Post hoc analysis indicated that the tissue response was significantly greater in Region A compared to Region B (Holm-Sidak, $p<0.001$) and was significantly greater in the cochleae implanted with the BDNF-SPs compared to the cochleae implanted with the Control-SPs (Holm-Sidak, $p=0.003$). Tissue response comprised of loose fibrotic tissue and new bone growth was restricted to a small proportion of the scala tympani near the site of implantation in the basal cochlear region. Further along the cochlea, in the middle turns the tissue response occupied an even smaller proportion of the scala tympani (Regions A and B FIGS. 1A-1B; FIGS. 2A-2F). Other cochlear compartments (the scala vestibuli and scala media) were devoid of any tissue response. These findings provide evidence that the SPs were well tolerated in vivo.

Example 6

Advantages of Supraparticle Carriers

The SP carrier system of the present disclosure has characteristics that make it uniquely suited for drug delivery to the cochlea. Firstly, the relatively large size of the SPs (~500 μm) allowed for easy handling during surgical implantation into the cochlea and ensured that SPs could not disperse away from the implantation site. Dispersal of smaller particles or cells from the cochlea to the central nervous system and/or the vestibular end organs is problematic because it reduces the therapeutic load to the target SGNs within the cochlea. Secondly, the SPs can provide sustained released of therapeutic neurotrophin (e.g. BDNF) meaning that longer durations of drug delivery are possible. Thirdly, the SPs can be loaded with high payloads of therapeutics and deliver therapeutic levels of these drugs. Fourthly, the immobilization of the BDNF in the pores of the SPs serves to protect the protein from denaturing in vivo, and thus maintains its bioactivity whereas protein instability over time is a problem when stored in mini-pumps (Zuccato and Cattaneo (2009) Nat Rev Neurol. 5, 311-322). This is important as neurotrophins have a relatively rapid half-life in vivo (approximately minutes when injected into plasma and approximately one hour when administered to the CSF). Fifthly, the SP technology enables the use of multiple therapeutic payloads that can potentially have release characteristics tailored for best effect for each drug type. Finally, the SP system offers the clinician the option of implanting the SPs into the cochlea, for instance along with a cochlear implant, or implanting them onto to round window membrane (external to the cochlea). The round window membrane is permeable to small molecules and drugs (Plontke et al. (2008) Otol Neurol. 29, 410-406; Plontke et al. (2007) Laryngoscope. 117, 1191-1198). A current clinical approach to deliver therapeutic compounds to the cochlea to treat hearing loss is to inject drugs into the middle ear cavity and rely on passive diffusion of the drug across the round window membrane. However, with this technique much of the drug is quickly lost down the eustachian tube, thus limiting the efficacy of the technique for delivering drugs to the cochlea. Similarly, there are restrictions in direct injections of drugs into the cochlea as volume limitations make it difficult to provide therapeutic levels of drugs with an iso-osmotic vehicle. If the volume it too high then most of the compound is lost outside of the cochlea or via the cochlear aqueduct. Accordingly, the sustained release profile provided by SPs suggests that implantation of drug-loaded SPs onto the round window membrane would be expected to improve drug entry into the cochlea.

Example 7

SP and Cochlear Implants

There is a strong correlation in SGN survival and cochlear implant performance with greater numbers of surviving SGNs resulting in better cochlear implant performance (Seyyedi et al. (2014) Otol Neurol. 35, 1446-1450). The development of clinically translatable neurotrophin delivery strategies that improve SGN survival and reduce the electrical thresholds would therefore likely lead to improvements in cochlear implant function in contemporary devices. Furthermore, ongoing SGN degeneration and cell loss is a significant impediment to the clinical implementation of current focussing strategies that aim to provide more precise neural activation within the cochlea (Goldwyn et al. (2010) Hear Res. 268, 93-104; Zhu et al. (2012) Hear Res. 283, 45-58). SP prevention or reduction in SGN loss, and promotion of SGN fibre regrowth, may improve the clinical outcomes of future stimulation strategies designed to improve the precision of neural activation within the cochlea. Accordingly, SPs can be implanted in combination with a cochlear device.

To further confirm SP and cochlear device compatibility, experiments were carried out in which deafened guinea pigs (n=3) were implanted with a cochlear implant along with SPs (n=6 into each ear) that were not loaded with drug. Animals received chronic electrical stimulation using a system similar to that described previously (Landry T G, Wise A K, Fallon J B, Shepherd R K (2011) Spiral ganglion neuron survival and function in the deafened cochlea following chronic neurotrophic treatment. Hear Res 282:303-313.)

Electrically-evoked auditory brainstem responses were measured at the time of implantation and after one month of chronic electrical stimulation, at the conclusion of the treatment period. Electrical thresholds were determined and showed that there was no difference between thresholds measured at the time of implantation to those measured after one month of chronic stimulation and SP implantation (FIG. 6). This data provides evidence that the SP delivery system is biologically compatible (no negative effects on the neural responsiveness to chronic stimulation) and suitable for clinical cochlear implant recipients.

Example 8

Distribution of Neurotrophins in the Cochlea

In order to establish the distribution of neurotrophin released by the supraparticles experiments were carried out using a radioactive tag (iodine 125) attached to neurotrophin-3. The radiolabelled neurotrophin was evident throughout a wide extent of the cochlea (into the apical cochlear regions) indicating that distribution was not localised to the basal turn (where the supraparticle was implanted) (FIG. 7B and 7C).

Next, 2 SPs produced by electrospraying were loaded with BDNF and placed inside the cochlea. Serial perilymph samples (1 ul samples) were obtained from the apex of the cochlea at three days and one week post implantation (sampling techniques described in Plontke et al. (2007) Laryngoscope. 117:1191-1198) and samples were analysed using an ELISA.

After 3 days peak BDNF perilymph concentration inside the cochlea 1707 ng/ml (n=2)

After 7 days peak BDNF perilymph concentration inside the cochlea 775 ng/ml (n=2)

Example 9

Pharmacokinetics

In vivo studies were carried out to determine the drug payload and clearance of neurotrophin delivered in a supraparticle implanted into the ear after 4 hr, 3 day and 7 days of implantation. The objective was to determine the amount of neurotrophin remaining in the cochlea over time.

1 SP containing radiolabelled neurotrophin-3 was implanted into each cochlea. Cochleae were harvested following 4 hrs (n=5), 3 d (n=7) or 7 d (n=4). Whole cochlear gamma counts were measured to determine the clearance of neurotrophin-3 over time. The remaining amount of neurotrophin-3 (% of loaded) and the total in μg is shown in FIG. 8. After 1 week of implantation each SP contained ~2 ug of neurotrophin-3 (~40%) of initial loaded amount.

Further experiments (n=2) were carried out to examine clearance of neurotrophin-3 following round window delivery. 3 days after implantation—whole cochlear measurements were again used to determine the clearance of neurotrophin-3 from the round window membrane. A similar level of clearance was observed using the round window compared to the intracochlear delivery site (47.4% of neurotrophin-3 remaining following round window delivery compared to 56% for intracochlear delivery).

These data show that extended release of neurotrophin-3 can be achieved with high levels of neurotrophin-3 still available even after 1 week of treatment.

Example 10

Nanoparticle Production

Mesoporous silica nanoparticles (MS-NP) ware produced using methods based on those described in Cui et al. 2015, ACS Nano, 9, 1571-1580. 1.1 g Cetyltrimethylammonium bromide (CTAB) was completely dissolved in 50 ml Milli-Q with stirring. 4.3 g of Poly(acrylic acid) solution (PAA, $M_w$=250 kDa, 35 wt % solution in water) was subsequently added with vigorous stirring for 20 mins at room temperature (25° C.) until a clear solution was obtained. 3.5 ml ammonium hydroxide solution (28-30%) was then added to the solution with vigorous stirring, resulting in a milky suspension. 4.46 ml of Tetraethyl orthosilicate (TEOS) was then added after stirring for 20 min. The solution was stirred for a further 15 min before transferring the mixture into a Teflon-sealed autoclave, which was left at 90° C. for 48 h.

The as-synthesized MS-NP were washed with ethanol once, water twice and ethanol twice and finally dried at 90° C. The organic templates were removed by calcination at 550° C. for 30 h.

Example 11

Starting Supraparticle Manufacturing Process—Process A

Mesoporous silica (MS) nanoparticles, were prepared according to Wang et al. (2010) Chem Mater. 22, 3829-3831. MS nanoparticles were dispersed in Milli-Q water with a particle concentration of 5 wt % and briefly sonicated to form a stable colloidal suspension. A 0.5 to 2.0 μL aliquot of the MS nanoparticle dispersion was then applied to a flat surface, which was pre-covered with a paraffin film. The droplets were dried under air flow to drive assembly of the MS nanoparticles into mesoporous silica supraparticles (capillary force MS-SPs) via capillary force action. The size of the capillary force MS-SPs was controlled by the volume of the nanoparticle dispersion applied in the droplet.

Under capillary force, the MS colloids self-assembled into a compact structure to form MS-SPs. The capillary force MS-SPs were then removed from the paraffin film and transferred into a ceramic container, and annealed at 923 K to enhance mechanical stability of the capillary force MS-SPs. Capillary force MS-SPs were then loaded with payload. About 1.33 μg protein was loaded per particle produced using process A.

The capillary force MS-SPs were shown to have a bimodal pore structure (2-3 nm and 15-30 nm) and the macropores within the capillary force MS-SP, the space between the densely packed nanoparticles, was 100-200 nm.

Example 12

Modified Manufacturing Process—Process B 80 mg of MS-NPs powder was added into 2 ml of alginic acid sodium salt solution (30 mg mL$^{-1}$ in water). The resulting solution was sonicated for 1 hour until the MS-NPs distributed uniformly in alginic acid sodium salt solution.

To form large pore MS-SPs ($^L$MS-SPs), the sonicated solution was added into a 3 mL plastic syringe and positioned in a syringe pump, with liquid being electrosprayed into a bath of calcium chloride solution (1 wt % prepared in water) using flow rates around 8 mL h$^{-1}$ (electrospray setup shown in FIG. 9). Droplet size was controlled by applying an electric field between the end of the tubing and the calcium chloride solution. The alginate beads MS-SPs ($^L$MS-SPs$^{alg}$) were collected from the calcium chloride bath and loaded with payload. Significantly enhanced drug-loading loading performance was observed for these particles ($^L$MS-SPs) compared to those produced by process A: about 7.8 μg protein per particle, with improved mechanical stability.

Example 13

Modified Manufacturing Process—Process C

MS-SPs ($^L$MS-SP$^{alg}$) were produced using the method described in Example 3. Alginic acid sodium salt was removed by calcination at 650° C. for 30 h. This step removed all organic components and left behind only the mesoporous silica nanoparticles (MS-SP) and trace amounts of calcium and sodium chloride. MS-SPs were then loaded with payload. Significantly enhanced drug-loading performance was observed for these particles compared to those produced by process A: about 7.8 μg protein per particle.

Supraparticles were also made from nanoparticles without pores (non porous $^N$MS-SPs$^{alg}$; $^N$MS-SPs$^{alg}$) and nanoparticles having pore sizes <2 nm (small pore MS-$^S$SPs$^{alg}$; $^S$MS-SPs$^{alg}$). When alginate was removed from these supraparticles drug-loading performance was significantly reduced (Table 1).

Maximal drug loading of MS-SP produced by process B and process C is summarized in Table 1.

TABLE 1

Loading of MS-SP produced by process B and process C

| Particle type | $q_{max}$ (ug/particle) |
| --- | --- |
| non porous $^N$MS-SPs$^{alg}$ | $q_{max}$ = 8.215 |
| non porous $^N$MS-SPs | $q_{max}$ = 2.009 |
| small pore $^S$MS-SPs$^{alg}$ | $q_{max}$ = 10.06 |
| small pore $^S$MS-SPs | $q_{max}$ = 2.802 |
| large pores $^L$MS-SPs$^{alg}$ | $q_{max}$ = 9.245 |
| large pores $^L$MS-SPs | $q_{max}$ = 7.843 |

Example 14

Supraparticle Release Properties

Lysozyme

FITC-lysozyme-loaded SPs were prepared for in vitro release studies by incubating sterilized SPs with 100 μL of FITC-lysozyme solution (0.2 mg mL$^{-1}$ in Milli-Q water). Lysozyme is a good model protein to mimic the neurotrophin BDNF (as lysozyme is cheap and readily available while BDNF is expensive) because it shares similar physicochemical properties (lysozyme, $M_w$=14.3 ±0.5 KDa, $R_H$=18.9 ±0.25 Å and pI=11; BDNF, $M_w$=13 KDa, $R_H$=24.0 ±3.2 Å and pI=10).

In vitro release profile of lysozyme loaded MS-SPs are shown in FIGS. 11A-11B. Release profiles of MS-SP produced by process A and C are similar. Although MS-SP produced by process C are loaded with significantly higher levels of labelled lysozyme. Payload release is significantly reduced for MS-SP produced by process B compared to MS-SP produced by processes A and C.

Zeta Potential

MS-SPs were then loaded with fluorescein-labelled lysozyme (FITC-lysozyme). As shown in FIG. 12, MS-SPs exhibited negative zeta potentials ranging from ~−7.6 mV to ~−33.9 mV as the pH value increased from 4 to 10. Positively charged lysozyme and BDNF can therefore be loaded into MS-SPs with the help of electrostatic driving forces. Confocal microscopy images (FIGS. 13A-13B) showed FITC-lysozyme loaded onto the surface of MS-SPs. However, as the size of the MS-SPs is quite large (hundreds of micrometers in diameter) standard laser scanning confocal microscopy is not suitable for imaging the internal structure of the SPs. However, upon fracturing the MS-SPs with a scalpel, the inside could be imaged and it was found that FITC-lysozyme was also observed in the porous internal structures of the MS-SPs (FIG. 13C).

Additional Assessment of Loading Capacity

The loading capacity for different types of SPs was then investigated using FITC-lysozyme at different loading concentrations with 3 days incubation time (FIGS. 10A-10D). In general, as the concentration of FITC-lysozyme increased, the amount of drug loading increased. The results show that the alginate-containing $^N$MS-SPs$^{alg}$, $^S$MS-SPs$^{alg}$ and $^L$MS-SPs$^{alg}$ had higher loading capacities than the alginate-removed $^N$MS-SPs, $^S$MS-SPs and $^L$MS-SPs (at comparable concentrations). This may be due to increased electrostatic interactions between positively charged FITC-lysozyme and negatively charged alginate around neutral pH value. Additionally, at low FITC-lysozyme loading concentration (<0.4 mg mL$^{-1}$), $^L$MS-SPs$^{alg}$ had a similar drug loading capacity as non porous MS-SPs$^{alg}$ and $^S$MS-SPs$^{alg}$, but when the concentration was higher (>0.4 mg mL$^{-1}$), more FITC-lysozyme could be loaded into $^L$MS-SPs$^{alg}$ compared to $^N$MS-SPs$^{alg}$ and $^S$MS-SPs$^{alg}$. For alginate-removed MS-SPs a similar trend was observed: $^L$MS-SPs could load more FITC-lysozyme than $^N$MS-SPs and $^S$MS-SPs. These results show that large porous structures (in $^L$MS-SPs and $^L$MS-SPs$^{alg}$) are key factors to improve drug loading, likely by providing additional surfaces and hence loading and capacity when outer particle surfaces and intra-particle areas (in the SP structures) have been fully saturated by the drug. Additionally, the loading capacity also depends on the diameter of MS-SPs where the bigger MS-SPs (1000 μm) had larger loading capacity than the smaller MS-SPs (200 μm) (FIGS. 14A-14D).

The experimentally determined maximum loading amount of FITC-lysozyme into $^N$MS-SPs and $^S$MS-SPs$^{alg}$ were about 3 μg per SP and 2 μg per SP respectively, which were significantly lower than $^L$MS-SPs with approximately 15 μg per SP (FITC-lysozyme concentration was 1.5 mg mL$^{-1}$, and loading time was 3 days). Besides, the experimentally determined maximum loading amount of FITC-lysozyme into $^N$MS-SPs and $^S$MS-SPs were about 2 μg per SP and 1 μg per SP respectively, which were also dramatically less than $^L$MS-SPs with approximately 10 μg per SP (FITC-lysozyme concentration was 5.0 mg mL$^{-1}$, and loading time was 3 days).

Figure 10A:
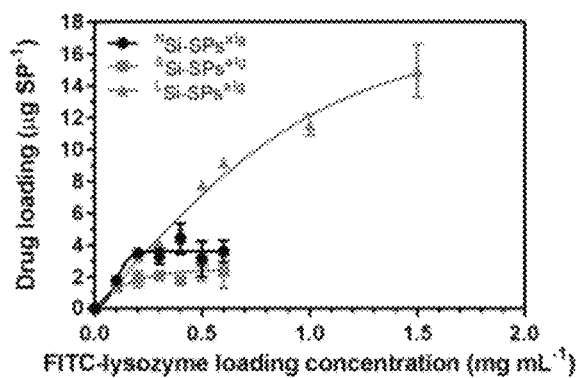
Figure 10B:
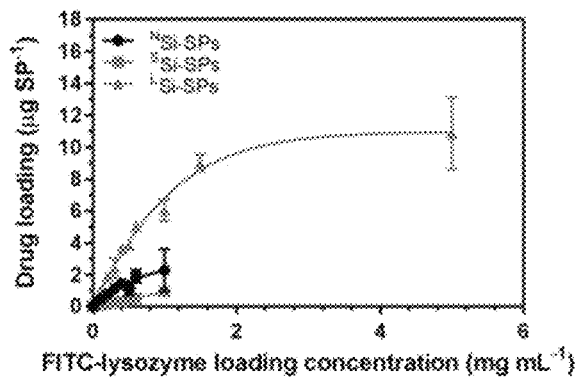
Figure 10C:
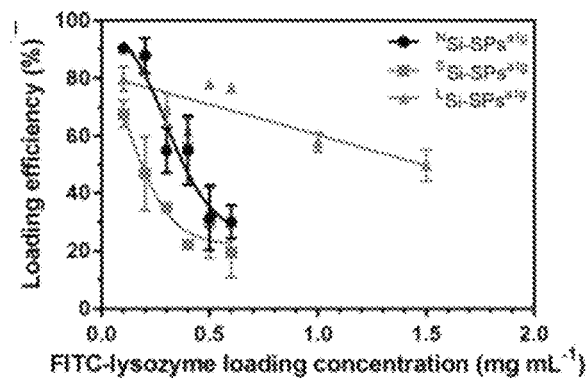
Figure 10D:
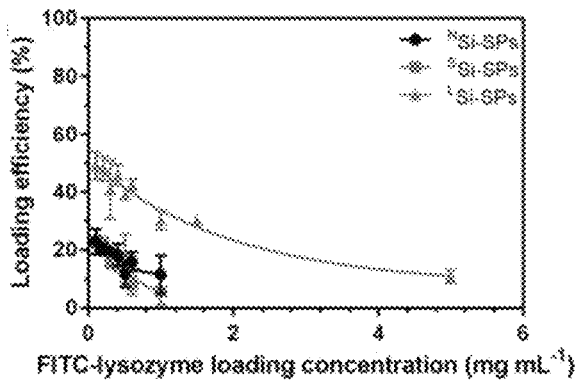

The drug loading efficiency of six different SPs is shown in FIGS. 10C and 10D. As the loading concentration of FITC-lysozyme increased, more FITC-lysozyme could be loaded into SPs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2017903829 filed 20 Sep. 2017, AU 2017903828 filed 20 Sep. 2017 and AU 2018902513 filed 11 Jul. 2018 the disclosures of which are incorporated herein by reference.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Clark G M, et al., "Surgery for an improved multiple-channel cochlear implant", Ann Otol Rhinol Laryngol 93:204-7, 1984

Clark G M, et al., "Surgical and safety considerations of multichannel cochlear implants in children", Ear and Hearing Suppl. 12:15S-24S, 1991

Dobie, R. A. (2005) Audiometric Threshold Shift Definitions: Simulations and Suggestions, Ear and Hearing 26(1) 62-77)

Goldwyn et al. (2010) Hear Res. 268, 93-104

Jaworek (2007) Powder Technology 176(1), 18-35

Kuncicky et al. (2007) Chem Mater. 19, 141-143

Kuncicky et al. (2008) Langmuir. 24, 1371-1380

Langer R (1990) Science. 249, 1527-1533

Landry et al. (2011) Hear Res. 282, 303-313

Park et al. (2006) J. Colloid Interface Sci. 298, 713-719

Plontke et al. (2008) Otol Neurol. 29, 410-406

Plontke et al. (2007) Laryngoscope. 117, 1191-1198

Rastogi et al. (2008) Adv Mater. 20, 4263-4268

Remington's Pharmaceutical Sciences (Mack Publishing Co. N.J. USA, 1991)

Seyyedi et al. (2014) Otol Neurol. 35, 1446-1450

Shepherd et al. (2005) J Comp Neurol. 486, 145-158

Shepherd et al. (2008) Hear Res. 242, 100-109

Tan et al. Adv. Mater. (2012) 24, 3362-3366

Wang et al. (2005) Angew. Chem. Int. Ed. 44, 2888

Wang et al. (2006) Adv. Mater. 18, 795

Wang et al. (2009) J. Mater. Chem. 19, 6451

Wang et al. (2010) Chem Mater. 22, 3829-3831
Wise et al. (2005) J Comp Neurol. 487, 147-165
Wise et al. (2010) Mol Ther. 18, 1111-1122
Wise et al. (2011) Neurotherapeutics. 8, 774-787
Xu et al. (1993) Hear Res. 70, 205-215
Yang and Pierstorff (2012) JALA. 17, 50-58
Zhu et al. (2012) Hear Res. 283, 45-58
Zuccato and Cattaneo (2009) Nat Rev Neurol. 5, 311-322

The invention claimed is:

1. A method of treating an auditory disorder in a human subject, the method comprising administering to an ear of the subject a supraparticle comprising a therapeutic payload, wherein the therapeutic payload comprises a neurotrophic factor, and wherein spiral ganglion neuron (SGN) survival is observed across a wide extent of the subject's cochlea, and wherein the auditory disorder comprises a hearing loss.

2. The method of claim 1, wherein the neurotrophic factor comprises brain derived neurotrophic factor (BDNF), nerve growth factor, neurotrophin-3, neurotrophin-4, ciliary neurotrophic factor (CNTF), Glial Cell Derived Neurotrophic Factor (GDNF). or IL-11.

3. The method of claim 1, wherein the therapeutic payload comprises a neurotrophin.

4. The method of claim 3, wherein the neurotrophin is neurotrophin-3.

5. The method of claim 3, wherein the supraparticle comprises between 1.5 µg and 15 µg of neurotrophin.

6. The method of claim 1, wherein the supraparticle comprises at least 2 different therapeutic payloads.

7. The method of claim 6, wherein the supraparticle comprises BDNF and at least one therapeutic payload selected from the group consisting of neurotrophin-3, neurotrophin-4, CNTF, and GDNF.

8. The method of claim 6, wherein the supraparticle comprises BDNF and a steroid or an antibiotic.

9. The method of claim 8, wherein the steroid is dexamethasone.

10. The method of claim 6, wherein the supraparticle comprises at least two therapeutic payloads, one therapeutic payload being a neurotrophic peptide.

11. The method of claim 1, wherein the hearing loss is characterised as noise induced hearing loss or sensorineural hearing loss (SNHL).

12. The method of claim 1, wherein the supraparticle is administered to the subject's middle ear cavity.

13. The method of claim 12, wherein the supraparticle is administered onto the subjects round window or oval window.

14. The method of claim 1, wherein the supraparticle is administered by implantation into the subject's cochlea.

15. The method of claim 1, wherein at least two supraparticles are administered to an ear of the subject.

16. The method of claim 15, wherein the at least two supraparticles have different payloads.

17. The method of claim 1, further comprising implanting a cochlear device.

18. The method of claim 1, wherein the hearing loss is categorised as partial and progressive or severe.

19. The method of claim 1, wherein the supraparticle is administered into the subject's inner ear.

20. The method of claim 19, wherein the supraparticle is administered onto the subject's basal turn of the cochlea.

* * * * *